United States Patent [19]

Nakane et al.

[11] Patent Number: 4,738,978
[45] Date of Patent: Apr. 19, 1988

[54] BISTHIOAMIDE-7-OXABICYCLOHEPTANE PROSTAGLANDIN ANALOGS

[75] Inventors: Masami Nakane, Aichi, Japan; Joyce Reid, Dayton, N.J.

[73] Assignee: E. R. Squibb & Sons, Inc., Princeton, N.J.

[21] Appl. No.: 928,947

[22] Filed: Nov. 10, 1986

[51] Int. Cl.⁴ .................. C07D 307/00; C07D 405/06; A61K 31/34; A61K 31/41
[52] U.S. Cl. .................... 514/382; 514/469; 548/253; 549/463
[58] Field of Search .............. 548/253; 549/463; 514/382, 469

[56] References Cited

U.S. PATENT DOCUMENTS

| | | | |
|---|---|---|---|
| 4,143,054 | 3/1979 | Sprague | 260/346.22 |
| 4,187,236 | 2/1980 | Sprague | 260/346.22 |
| 4,220,594 | 9/1980 | Sprague | 260/345.9 |
| 4,228,180 | 10/1980 | Sprague | 424/285 |
| 4,254,044 | 3/1981 | Sprague | 260/347.8 |
| 4,416,896 | 11/1983 | Nakane et al. | 424/285 |
| 4,456,615 | 6/1984 | Nakane et al. | 424/285 |
| 4,456,617 | 6/1984 | Nakane et al. | 424/285 |
| 4,525,479 | 6/1985 | Das et al. | 514/469 |
| 4,638,012 | 1/1987 | Nakane | 514/469 |
| 4,647,573 | 3/1987 | Nakane | 514/382 |

FOREIGN PATENT DOCUMENTS

| | | |
|---|---|---|
| 0043292 | 8/1982 | European Pat. Off. . |
| 0082646 | 6/1983 | European Pat. Off. . |
| 2039909 | 8/1980 | United Kingdom . |

*Primary Examiner*—Robert Gerstl
*Attorney, Agent, or Firm*—Lawrence S. Levinson; Burton Rodney

[57] ABSTRACT

Bisthioamide-7-oxabicycloheptane prostaglandin analogs are provided having the structural formula

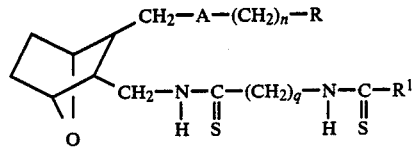

wherein A is —CH=CH— or —CH$_2$—CH$_2$—; n is 1 to 5; R is CO$_2$H, CO$_2$lower alkyl or

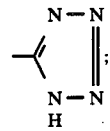

q is 1 to 12; and R$^1$ is H, lower alkyl, lower alkenyl, lower alkynyl, aryl, arylalkyl, lower alkoxy, aryloxy, arylalkyloxy, amino, alkylamino arylamino, arylalkylamino, lower alkyl-S-aryl-S-, arylalkyl-S-,

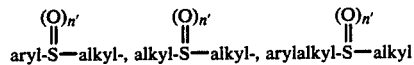

(wherein n' is 0, 1 or 2), alkylaminoalkyl, arylaminoalkyl, arylalkylaminoalkyl, alkoxyalkyl, aryloxyalkyl or arylalkoxyalkyl.

The compounds are cardiovascular agents useful, for example, in the treatment of thrombotic disease.

14 Claims, No Drawings

BISTHIOAMIDE-7-OXABICYCLOHEPTANE PROSTAGLANDIN ANALOGS

DESCRIPTION OF THE INVENTION

The present invention relates to bisthioamide-7-oxabicycloheptane prostaglandin analogs which are cardiovascular agents useful, for example, in the treatment of thrombotic disease. These compounds have the structural formula

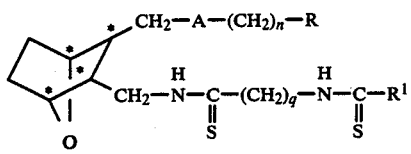

including all stereoisomers thereof, wherein A is —CH=CH— or —CH$_2$—CH$_2$—; n is 1 to 5; R is CO$_2$H, CO$_2$ lower alkyl or

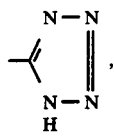

q is 1 to 12; and R$^1$ is H, lower alkyl, lower alkenyl, lower alkynyl, aryl, arylalkyl, lower alkoxy, arylalkyloxy, aryloxy, amino, alkylamino, arylalkylamino, arylamino, lower alkyl-S-, aryl-S-, arylalkyl-S-,

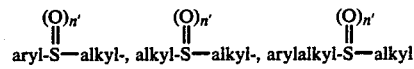

(wherein n' is 0, 1 or 2), alkylaminoalkyl, arylaminoalkyl, arylalkylaminoalkyl, alkoxyalkyl, aryloxyalkyl or arylalkoxyalkyl.

The term "lower alkyl" or "alkyl" as employed herein alone or as part of another group includes both straight and branched chain hydrocarbons, containing 1 to 12 carbons in the normal chain, preferably 1 to 7 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including a halo-substituent, such as F, Br, Cl or I or CF$_3$, an alkoxy substituent, an aryl substituent, an alkylaryl substituent, a haloaryl substituent, a cycloalkyl substituent, an alkylcycloalkyl substituent, hydroxy, and alkylamino substituent, an alkanoylamino substituent, an arylcarbonylamino substituent, a nitro substituent, a cyano substituent, a thiol substituent or an alkylthio substituent.

The term "cycloalkyl" as employed herein alone or as part of another group includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 or 2 halogens, 1 or 2 lower alkyl groups, 1 or 2 lower alkoxy groups, 1 or 2 hydroxy groups, 1 or 2 alkylamino groups, 1 or 2 alkanoylamino groups, , 1 or 2 arylcarbonylamino groups, 1 or 2 amino groups, 1 or 2 nitro groups, 1 or 2 cyano groups, 1 or 2 thiol groups, and/or 1 or 2 alkylthio groups.

The term "aryl" or "Ar" as employed herein refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be 1 or 2 lower alkyl groups, halogens (Cl, Br or F), 1 or 2 lower alkoxy groups, 1 or 2 hydroxy groups, 1 or 2 alkylamino groups, 1 or 2 alkanoylamino groups, 1 or 2 arylcarbonylamino groups, 1 or 2 amino groups, 1 or 2 nitro groups, 1 or 2 cyano groups, 1 or 2 thiol groups, and/or 1 or 2 alkylthio groups.

The term "aralkyl", "aryl-alkyl" or "aryl-lower alkyl" as used herein alone or as part of another group refers to lower alkyl groups as discussed above having an aryl substituent, such as benzyl.

The term "lower alkoxy", "alkoxy", or "aryloxy" or "aralkoxy" as employed herein alone or as part of another group includes any of the above lower alkyl, alkyl, aralkyl or aryl groups linked to an oxygen atom.

The term "lower alkylthio", "alkylthio", "arylthio" or "aralkylthio" as employed herein alone or as part of another group includes any of the above lower alkyl, alkyl, aralkyl or aryl groups linked to a sulfur atom.

The term "lower alkylamino", "alkylamino", "arylamino", "arylalkylamino" as employed herein alone or as part of another group includes any of the above lower alkyl, alkyl, aryl or arylalkyl groups linked to a nitrogen atom.

The term "alkanoyl" as used herein as part of another group refers to lower alkyl linked to a carbonyl group.

The term "lower alkenyl" as used herein by itself or as part of another group refers to straight or branched chain radicals of 2 to 12 carbons, preferably 2 to 6 carbons in the normal chain, which include one double bond in the normal chain, such as 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl and the like.

The term "lower alkynyl" as used herein by itself or as part of another group refers to straight or branched chain radicals of 2 to 12 carbons, preferably 2 to 6 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like.

The term (CH$_2$)$_n$ includes straight or branched chain radicals having from 1 to 5 carbons in the normal chain and may contain one or more lower alkyl and/or halogen substituents. Examples of (CH$_2$)$_n$ groups include

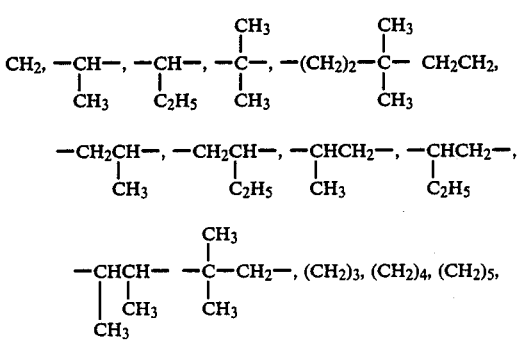

-continued

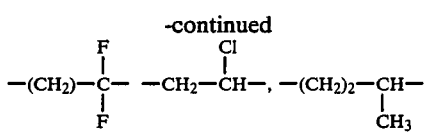

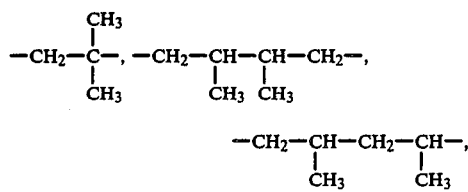

and the like.

The term $(CH_2)_q$ includes straight or branched chain radicals having from 1 to 12 carbons in the normal chain and includes any of the above examples of $(CH_2)_n$ groups as well as $(CH_2)_6$, $(CH_2)_7$, $(CH_2)_8$, $(CH_2)_9$, $(CH_2)_{10}$, $(CH_2)_{11}$, $(CH_2)_{12}$, and may be unsubstituted or substituted by one or more halo, hydroxy, alkoxy, amine, alkylamine, arylamine, amide, thioamide, thiol, alkylthio, arylthio, cyano or nitro groups.

The term "amide" refers to the group

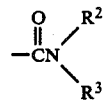

wherein $R^2$ and $R^3$ are independently hydrogen, lower alkyl or aryl.

The term "halogen" or "halo" as used herein refers to chlorine, bromine, fluorine, iodine and $CF_3$, with chlorine or fluorine being preferred.

Preferred are those compounds of formula I wherein A is a —CH=CH—, n is 1 or 4, R is $CO_2H$ R is H, $(CH_2)_q$ is —$CH_2$— and $R^1$ is lower alkyl such as pentyl, hexyl, or heptyl, or lower alkoxy such as pentoxy, lower alkylamino, such as pentylamino or arylthioalkyl, such as phenylthiomethyl.

The compounds of formula I of the invention may be prepared according to the following reaction sequence and as described below.

A. Where $R^1 \neq NH_2$

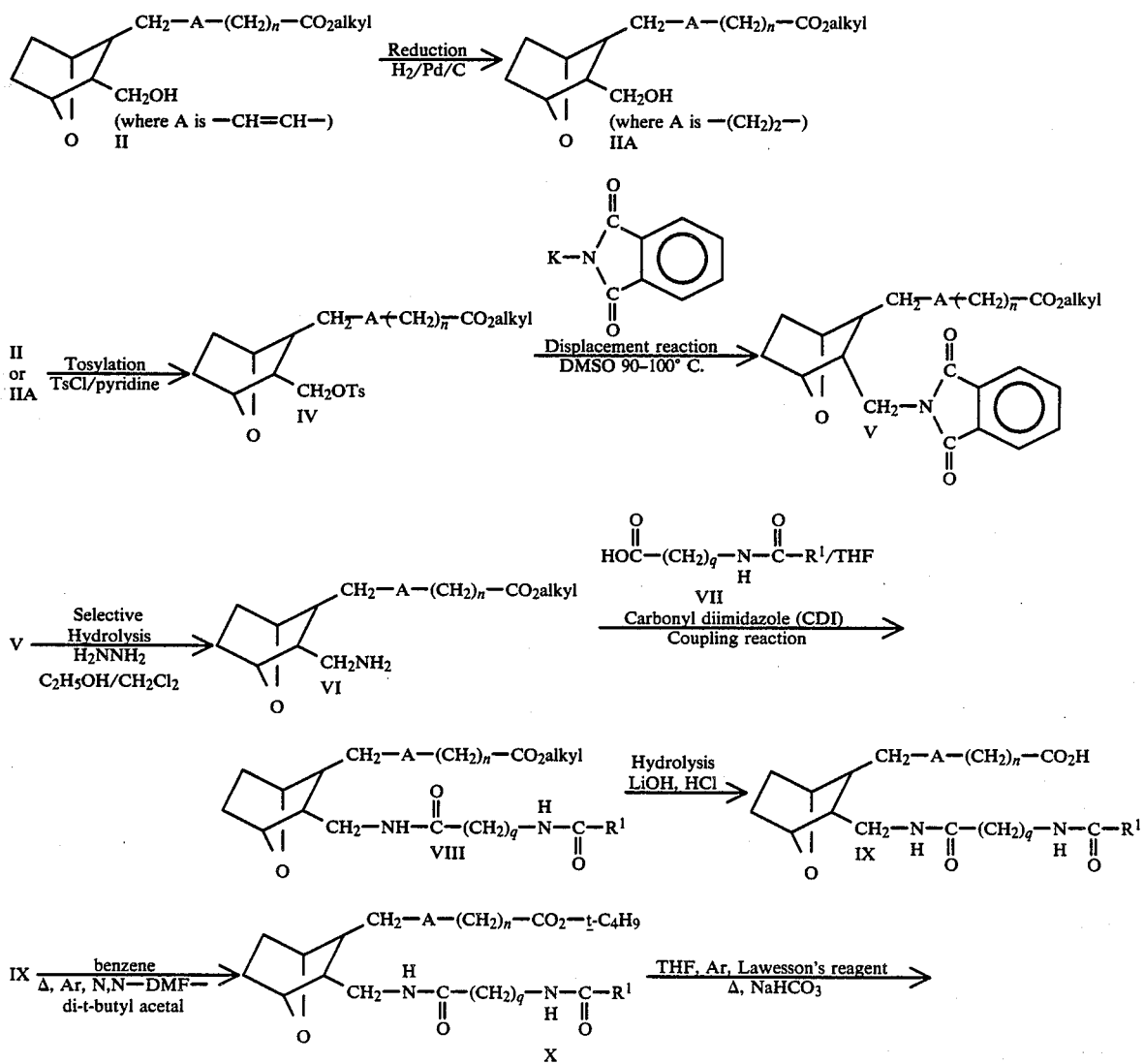

4,738,978
-continued
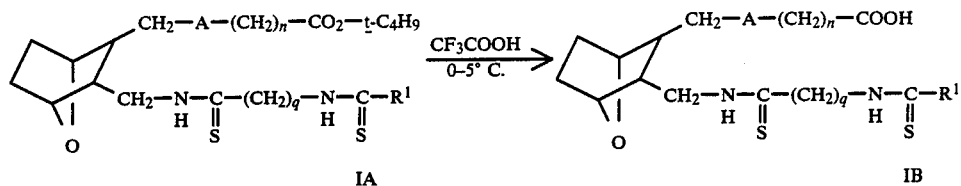
B. Where R¹ is NH₂
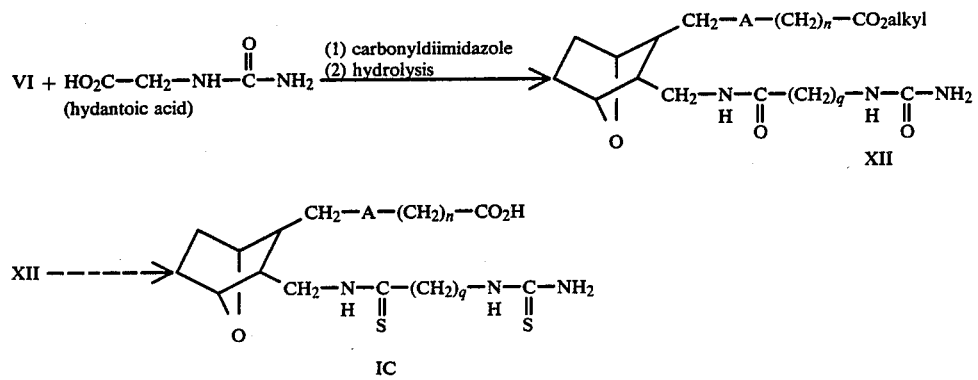
C. Where R is ![tetrazole] and A is CH=CH
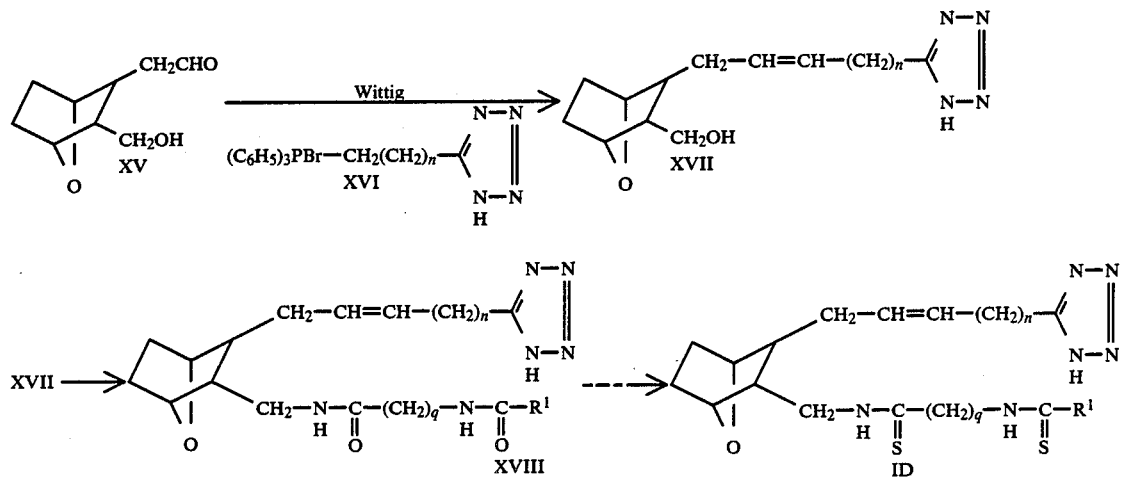
D. Where R is ![tetrazole] and A is (CH₂)₂
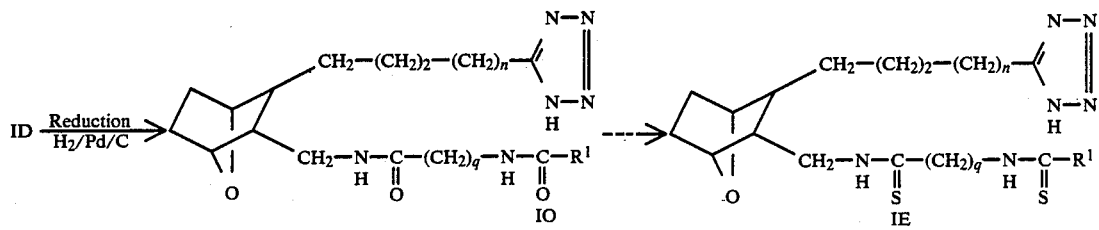

As seen in reaction sequence "A", compounds of the invention where $R^1$ is other than $NH_2$, that is,

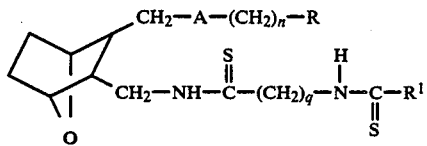  IA are prepared by tosylating the lower alkyl ester containing the hydroxymethyl group, that is, compound II or IIA, (prepared as described in U.S. Pat. No. 4,143,054) by reacting II or IIA with tosyl chloride in the presence of pyridine to form the corresponding tosylate IV which is subjected to a displacement reaction by dissolving IV in dimethylsulfoxide and heating to 90° to 100° C. in the presence of potassium phthalimide to form the phthalimide V. The phthalimide V is then made to undergo selective hydrolysis by dissolving V in methylene chloride and ethanol under an inert atmosphere such as argon and reacting with anhydrous hydrazine to form the amine VI

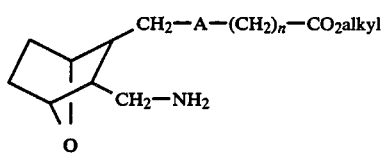  VI

The amine VI is then subjected to a CDI coupling reaction by reacting VI or VIA with acid VII

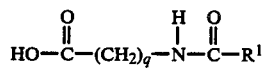  VII in the presence of an inert organic solvent such as tetrahydrofuran and carbonyl diimidazole under an inert atmosphere, such as argon, employing a molar ratio of VI:VII of within the range of from about 1:1 to about 1:1.2, to form the amide ester compound VIII

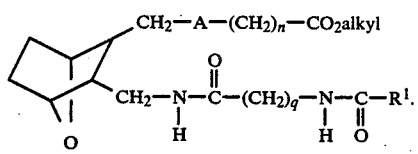  VIII

The ester VIII is converted to the free acid, that is, to

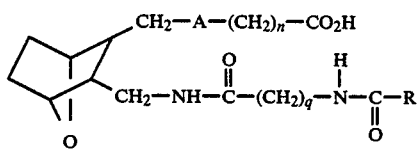  IX by treating the ester with a base, such as lithium hydroxide, sodium hydroxide or potassium hydroxide to form the corresponding alkali metal salt, followed by neutralization with an acid, such as dilute HCl or oxalic acid to form the acid IX.

Acid IX is dissolved in benzene or other suitable inert organic solvent under an inert atmosphere, such as argon, and is then treated with N,N-dimethylformamide-di-t-butyl acetal

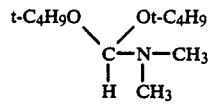

while heating under reflux to form ester X

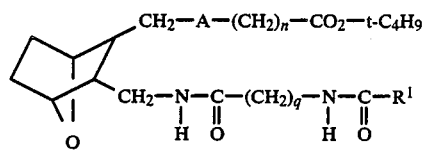  X

Ester X is then dissolved in tetrahydrofuran, or other suitable inert organic solvent under an inert atmosphere such as argon. Lawesson's reagent (that is [2,4-bis(4-methoxyphenyl)-1,3 dithia-2,4-diphosphetane-2,4-disulfide]) is added and the mixture is heated under reflux to form ester compound of the invention IA

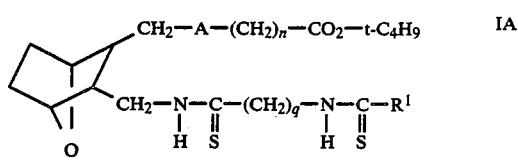  IA

Ester IA is converted to the free acid of the invention IB by treating IA with trifluoroacetic acid at 0°-5° C. to form IB

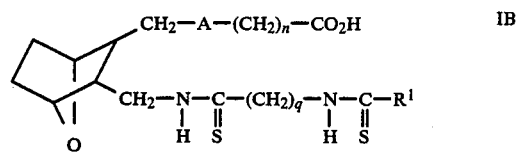  IB

In reaction sequence "B" compounds of the invention wherein $R^1$ is $NH_2$, that is IC

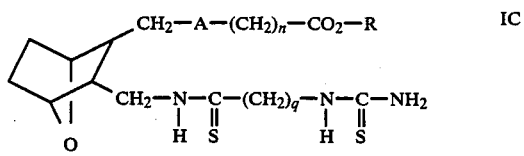  IC may be prepared by reacting amine VI with hydantoic acid in the presence of carbonyldiimidazole and then hydrolyzing the resulting product to form XII which is used in place of ester VIII in reaction sequence "A" to form IC.

Compounds of the invention wherein R is tetrazole

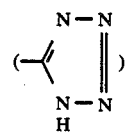

and A is CH=CH are prepared as described in reaction sequence "C" wherein alcohol XV

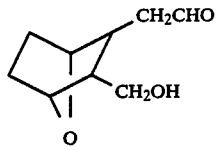   XV (prepared as described in U.S. Pat. No. 4,143,054) is reacted with a Wittig reagent of the structure XVI

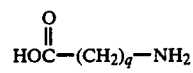   XVI in the presence of a base, such as potassium t-butoxide or sodium hydride-dimethyl sulfoxide employing a molar ratio of XV:XVI of within the range of from about 1:1 to about 0.2:1 to form the hydroxymethyl compound XVII

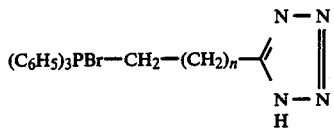   XVII which may then be employed in reaction sequences "A" and "B" in place of compounds II or VI to form compounds of the invention ID where A is —CH=CH— or IE where A is (CH$_2$)$_2$

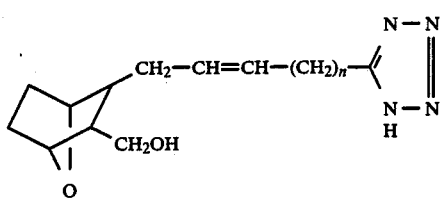   ID or IE

Alternatively, compound IE may be prepared by reducing compound ID by treating with H$_2$ in the presence of palladium on charcoal.

To form the sulfinyl and/or sulfonyl analogs of compounds of formula I wherein R$^1$ is -alkyl-S-aryl, alkyl-S-alkyl, or -alkyl-S-alkylaryl, formulae IX and XII compounds are subjected to oxidation, for example, by reacting same with sodium periodate or potassium monopersulfate (oxone) in the presence of methanol to form the sulfinyl derivative and/or sulfonyl derivative. Mixtures thereof may be separated by chromatography or other conventional separation procedures. The resulting sulfinyl and/or sulfonyl compounds are then employed in place of compound IX in sequence "A" or XII in sequence "B" to form the sulfinyl and/or sulfonyl compounds of the invention.

The starting acid VII

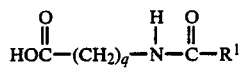   VII may be prepared by reacting the amino acid A $$HOC-(CH_2)_q-NH_2$$   A with acid chloride B $$Cl-C-R^1$$   B in the presence of a strong base such as NaOH and water.

The compounds of this invention have four centers of asymmetry as indicated by the asterisks in formula I. However, it will be apparent that each of the formulae set out above which do not include asterisks still represent all of the possible stereoisomers thereof. All of the various stereoisomeric forms are within the scope of the invention.

The various stereoisomeric forms of the compounds of the invention, namely, cis-exo, cis-endo and all trans forms and stereoisomeric pairs may be prepared as shown in the working Examples which follow and by employing starting materials following the procedures as outlined in U.S. Pat. No. 4,143,054. Examples of such stereoisomers are set out below.

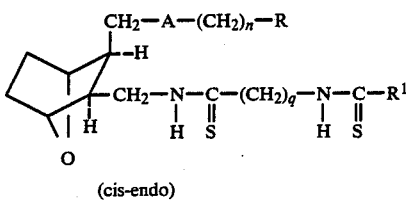   Ia (cis-endo)

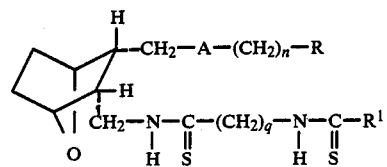   Ib (cis-exo)

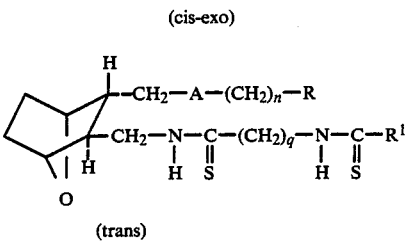   Ic (trans)

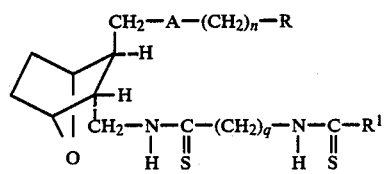   Id (trans)

The nucleus in each of the compounds of the invention is depicted as

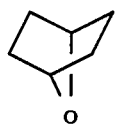

for matter of convenience; it will also be appreciated that the nucleus in the compounds of the invention may be depicted as

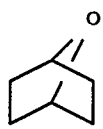

The compounds of this invention are cardiovascular agents useful as platelet aggregation inhibitors, such as in inhibiting arachidonic acid-induced platelet aggregation, e.g., for treatment of thrombotic disease such as coronary or cerebral thromboses, and in inhibiting bronchoconstriction. They are also selective thromboxane $A_2$ receptor antagonists and synthetase inhibitors, e.g., having a vasodilatory effect for treatment of myocardial ischemic disease, such as angina pectoris.

The compounds of this invention may also be used in combination with a cyclic AMP phosphodiesterase (PDE) inhibitor such as theophylline or papaverine in the preparation and storage of platelet concentrates.

The compounds of the invention can be administered orally or parenterally to various mammalian species known to be subject to such maladies, e.g., humans, cattle, horses, cats, dogs, and the like in an effective amount within the dosage range of about 1 to 100 mg/kg, preferably about 1 to 50 mg/kg and especially about 2 to 25 mg/kg on a regimen in single or 2 to 4 divided daily doses.

The active substance can be utilized in a composition such as tablet, capsule, solution or suspension containing about 5 to about 500 mg per unit of dosage of a compound or mixture of compounds of formula I. They may be compounded in conventional matter with a physiologically acceptable vehicle or carrier, excipient, binder, preservative, stabilizer, flavor, etc. as called for by accepted pharmaceutical practice. Also as indicated in the discussion above, certain members additionally serve as intermediates for other members of the group.

The compounds of the invention may also be administered topically to treat peripheral vascular diseases and as such may be formulated as a cream or ointment.

The following Examples represent preferred embodiments of the present invention. Unless otherwise indicated, all temperatures are expressed in degrees Centigrade.

EXAMPLE 1

[1S-[1α,2β(5Z),3β,4α]]-7-[3-[[[1-Thioxo-2[(1-thiox-oheptyl)amino]ethyl]amino]methyl]-7-oxabicyclo[2.2.1]hept-2-yl]-5-heptenoic acid, t-butyl ester

A. [1S-[1α,2β(5Z),3β,4α]]-7-[3-[[[[(1-Oxoheptyl)amino]acetyl]amino]methyl]-7-oxabicyclo[2.2.1]hept-2-yl]-5-heptenoic acid, methyl ester A(1) [1S-[1β,2α(5Z),3α,4β]]-7-[3-(Tosyloxymethyl)-7-oxabicyclo[2.2.1]hept-2-yl]-5-heptenoic acid, methyl ester Tosyl chloride (4.256 g, 22.4 mmol) dissolved in $CH_2Cl_2$ (30 ml) was added dropwise to a magnetically stirred solution of [1S-[1α,2β(5Z),3β,4α]]-7-[3-(hydroxymethyl)-7-oxabicyclo[2.2.1]hept-2-yl]-5-heptenoic acid, methyl ester (prepared as described in U.S. Pat. No. 4,143,054 (3 g, 11.2 mmol) in pyridine (30 ml) at 0° C. After completion of the addition, the reaction was warmed to room temperature and stirred overnight. The reaction was poured into ice/$H_2O$ and stirred for 30 minutes. The products were extracted with EtOAc (80 ml×3). The combined EtOAc layers were washed with 3N-HCl (40 ml×3), saturated $NaHCO_3$, brine and dried over $MgSO_4$. Filtration and evaporation of solvent gave a white solid, which was crystallized from isopropyl ether to give the corresponding title tosylate in the form of needle crystals (4.23 g, 89%), m.p. 68°-70° C.

A(2) [1S-[1β,2α(5Z),3α,4β]]-7-[3-(Aminomethyl)-7-oxabicyclo[2.2.1]hept-2-yl]-5-heptenoic acid, methyl ester The title A(1) tosylate was subjected to a Gabriel synthesis to form the corresponding amino compound as described below.

The potassium phthalimide used was purified prior to use by boiling 5 g thereof with 9 ml acetone for 15 minutes, filtering while hot and washing with 5 ml acetone. The remaining solid was dried in vacuo for 6 hours at 100° C. prior to use.

The title A(1) tosylate (8.11 g, 19.2 mmol) and purified potassium phthalimide (6.4 g, 34.6 mmol, 1.8 equiv.) in dimethylsulfoxide (70 ml, Burdick & Jackson) were heated at 90°–100° C. for 2½ hours (checked by TLC, $Et_2O$-pet ether 2:1, no tosylate remaining). After cooling to room temperature, water (90 ml) was added. Material began precipitating. The mixture was poured into ice water (~350 ml) and stirred 30 minutes. The straw colored solid was harvested by filtration and washed with more water. The solid was dissolved in warm ethyl acetate (150 ml), washed with water (3×50 ml), dried ($MgSO_4$), filtered and freed of solvent in vacuo. The remaining solid (7.88 g) was recrystallized from isopropyl ether (~150 ml) to give corresponding phthalimide (6.35 g, 83%) TLC. $Et_2O$-hexane 2:1, UV+vanillin $R_f$=0.38, trace 0.09.

The above phthalimide (5.05 g, 13.8 mmol) was dissolved in distilled $CH_2Cl_2$ (24 ml) and distilled ethanol (104 ml) in an argon atmosphere. Anhydrous hydrazine (0.78 ml, 25.6 mmol) was added. The mixture was stirred at room temperature. After 8 hours an additional 0.2 ml of hydrazine was added and the mixture was stirred an additional 15 hours at room temperature. A white solid was removed by filtration and washed with more $CH_2Cl_2$. The filtrate was taken to dryness in vacuo (on the pump at end). Cold 0.5N HCl solution (80 ml) was added. A small amount of white solid was removed by filtration and washed with additional 0.5N HCl solution (80 ml). The acidic solution was washed with ether (2×100 ml) and then basified with solid $K_2CO_3$. The amine was extracted into $CHCl_3$ (3×100 ml), dried ($MgSO_4$) and freed of solvent in vacuo leaving a yellow oil. Ether (100 ml) was added to this oil. Some solid was insoluble. After cooling in an ice bath, the solid was removed by filtration. The solvent was removed from the filtrate in vacuo leaving title amine as a pale yellow oil (2.441 g, 71%). NMR spectra and TLC indicated some minor impurities. The material was used without further purification.

B.
[1S-[1α,2β(5Z),3β,4α]]-7-[3-[[[[(1-Oxoheptyl)amino]acetyl]amino]methyl]-7-oxabicyclo[2.2.1]hept-2-yl]-5-heptenoic acid, methyl ester B(1) 2-(Heptanoylamino)acetic acid Glycine (1.5 g, 20 mmol) and heptanoyl chloride (22 mmol) were reacted in the presence of NaOH (40 mmol) in a mixture of water and ether using the method described in Example 5. The crude product was recrystallized from EtOAc (30 ml) to give title compound (2.71 g, 72%), m.p. 98°–100° C.

B(2) [1S-[1α,2β(5Z),3β,4α]]-7-[3-[[[[(1-Oxoheptyl)amino]acetyl]amino]methyl]-7-oxabicyclo[2.2.1]hept-2-yl]-5-heptenoic acid, methyl ester Part B(1) compound (187 mg, 1 mmol) was dissolved in distilled THF (8 ml) in an argon atmosphere and cooled in an ice bath. Carbonyldiimidazole (CDI) (162 mg, 1 mmol) was added and the mixture was stirred cold for 1 hour and then for 1 hour at room temperature. After cooling in an ice bath, a solution of chiral amine prepared in Part A(2) (267 mg, 1 mmol) in THF (3 ml) was added. The ice bath was removed and the mixture was stirred overnight at room temperature. The solvent was removed in vacuo. $CHCl_3$ (35 ml) was added to the residue. The solution was washed with 1N HCl (15 ml), 1N NaOH solution (15 ml) and $H_2O$ (15 ml), dried ($MgSO_4$) and freed of solvent in vacuo leaving an oil (424 mg). This was chromatographed on silica gel (20 g, Baker for flash chromatography), eluting with EtOAc and 2% MeOH in EtOAc to give the title ester compound as an oil (270 mg, 62%). TLC: silica gel, 5% MeOH in EtOAc, vanillin; $R_f$=0.45.

C.
[1S-[1α,2β(5Z),3β,4α]]-7-[3-[[[[(1-Oxoheptyl)amino]acetyl]amino]methyl]-7-oxabicyclo[2.2.1]hept-2-yl]-5-heptenoic acid The Part B(2) methyl ester (265 mg, 0.607 mmol) was dissolved in distilled THF (25 ml) and water (5 ml) in an argon atmosphere. 1N LiOH solution (5.6 ml) was added and the mixture was stirred at room temperature 4 hours. After neutralizing with 1N HCL solution (5.6 ml) and addition of solid KCl, the layers were separated. The aqueous layer was extracted with $CHCl_3$ (3×25 ml). The combined organic layers (THF+$CHCl_3$) were washed with saturated NaCl solution (15 ml), dried ($MgSO_4$) and freed of solvent in vacuo leaving an oil (242 mg). The crude crystalline product was recrystallized from EtOAc (4 ml) to give title acid (204 mg, 80%), m.p. 114°–116° C.

TLC: Silica gel, 10% MeOH in $CH_2Cl_2$, vanillin, $R_f$=0.40.

$[α]_D$= −6.6° (C=1.15, MeOH).

Anal Calcd for $C_{23}H_{38}O_5N_2$; C, 65.37; H, 9.06; N, 6.42. Found: C, 65.38; H, 9.01; N, 6.64.

D.
[1S-[1α,2β(5Z),3β,4α]]-7-[3-[[[1-Thioxo-2-[(1-thioxoheptyl)amino]ethyl]amino]methyl]-7-oxabicyclo[2.2.1]hept-2-yl]-5-heptenoic acid, t-butyl ester D(1) [1S-[1α,2β(5Z),3β,4α]]-7-[3-[[[1-Oxo-2-[(1-oxoheptyl)amino]ethyl]-amino]methyl]-7-oxabicyclo[2.2.1]hept-2-yl]-5-heptenoic acid, t-butyl ester Part C acid (507 mg, 1.2 mmol) was partially dissolved in distilled benzene (10 ml) in an argon atmosphere. After heating to reflux, N,N-dimethylformamide-di-t-butyl acetal (1.15 ml, ~970 mg, 4.8 mmol) was added dropwise in 45 minutes while continuing to heat under reflux. One hour after addition was complete, additional N,N-dimethylformamide-di-t-butyl acetal (0.35 ml) was added dropwise in 30 minutes and heating was continued an additional 60 minutes. After cooling, the mixture was diluted with ether (30 ml) and washed with 1N NaOH (15 ml) and saturated NaCl solution (15 ml). The solution was dried ($MgSO_4$), filtered and freed of solvent in vacuo leaving title ester (508.5 mg, 88.5%).

TLC: silica gel, 5% MeOH in $Et_2O$, vanillin $R_f$=0.34.

D(2) [1S-[1α,2β(5Z),3β,4α]]-7-[3-[[[1-Thioxo-2-[(1-thioxoheptyl)amino]ethyl]amino]methyl]-7-oxabicyclo[2.2.1]hept-2-yl]-5-heptenoic acid, t-butyl ester Part D(1) ester (505 mg, 1.05 mmol) was dissolved in distilled tetrahydrofuran (15 ml) in an argon atmosphere. Lawesson's reagent (286 mg, 0.7 mmol) was added and the mixture was heated under reflux for 2 hours 20 minutes. After cooling to 0°–5° C., saturated $NaHCO_3$ solution (15 ml) was added slowly. The cooling bath was removed and stirring was continued 15 minutes. Ether (60 ml) was added and the layers were separated. The aqueous layer was reextracted with ether (30 ml). The combined organic layers were washed with saturated $NaHCO_3$ solution (20 ml) and water (20 ml), dried ($MgSO_4$) and freed of solvent in vacuo leaving a yellow-orange oil (488 mg). This was chromatographed on silica gel (20 g, Baker for flash chromatography) eluting with EtOAc-hexane 1:4 to give title ester (239 mg, 44.6%) as a yellow oil.

TLC: silica gel, EtOAc-hexane 1:2, UV & vanillin, $R_f$=0.51.

EXAMPLE 2

[1S-[1α,2β(5Z),3β,4α]]-7-[3-[[[1-Thioxo-2-[(1-thioxoheptyl)amino]ethyl]amino]methyl]-7-oxabicyclo[2.2.1]hept-2-yl]-5-heptenoic acid The Example 1 ester (239 mg, 0.468 mmol) was cooled in an ice bath and treated with precooled distilled trifluoroacetic acid (7 ml). The solution was stirred at 0°–5° C. for 75 minutes. The trifluoroacetic acid was removed in vacuo leaving an oil (252 mg). This was chromatographed on SiliCAR CC4 eluting with 1.2% MeOH in $CH_2Cl_2$ to give title acid (129 mg, 60%) as an amber oil.

TLC: silica gel, 5% MeOH in $CH_2Cl_2$, UV+vanillin, $R_f$=0.26.

$[α]_D$= +7.7° (c=1.7, MeOH).

Anal Calcd for $C_{23}H_{38}O_3N_2S_2 \cdot 0.4H_2O$: C, 59.80; H, 8.47; N, 6.07; S, 13.88. Found: C, 59.65; H, 8.13; N, 6.00; S, 13.88.

EXAMPLE 3

[1S-[1α,2β(5Z),3β,4α]]-7-[3-[[[1-Thioxo-2-[(butylaminothiocarbonyl)amino]ethyl]amino]methyl]-7-oxabicyclo[2.2.1]hept-2-yl]-5-heptenoic acid

A.

[1S-[1α,2β(5Z),3β,4α]]-7-[3-[[[[(Butylamino)carbonyl]amino]acetyl]amino]methyl]-7-oxabicyclo[2.2.1]hept-2-yl]-5-heptenoic acid A(1) N-[(Butylamino)carbonyl]glycine, ethyl ester Glycine ethyl ester•HCl (5.58 g, 40 mmol) was suspended in distilled $CH_2Cl_2$ (20 ml). After cooling in an ice bath, distilled $Et_3N$ (6.13 ml, 44 mmol) was added. Distilled n-butyl isocyanate (4.95 ml, 44 mmol) was added. The cooling bath was removed and the mixture was left stirring overnight at room temperature. Additional $Et_3N$ (3.05 ml) was added and the mixture was stirred 3 more hours. After diluting with more $CH_2Cl_2$, the solution was washed with water (50 ml), 1N HCl (50 ml), saturated $NaHCO_3$ solution (50 ml) and water (50 ml). After drying ($MgSO_4$), the solvent was removed in vacuo leaving the title compound (7.641 g, 94%) which slowly crystallized. This was used without further purification.

A(2) N-[(Butylamino)carbonyl]glycine

Part A(1) ethyl ester (3.378 g, 16.7 mmol) was dissolved in distilled THF (100 ml) and treated with 1N LiOH solution (40 ml). After stirring overnight at room temperature and acidifying with concentrated HCl, solid KCl was added. The layers were separated. The aqueous layer was reextracted with EtOAc (3×50 ml). The combined organic layers (THF and EtOAc) were washed with saturated NaCl solution (25 ml), dried ($MgSO_4$), and freed of solvent in vacuo leaving the title compound, as a white solid (2.81 g, 97%).

A(3) [1S-[1α,2β(5Z),3β,4α]]-7-[3-[[[[(Butylamino)carbonyl]amino]acetyl]amino]methyl]-7-oxabicyclo[2.2.1]hept-2-yl]-5-heptenoic acid, methyl ester Part A(2) compound (174.2 mg, 1 mmol) was partially dissolved in distilled THF (8 ml) in an argon atmosphere. After cooling in an ice bath, carbonyl diimidazole (CDI) (162 mg, 1 mmol) was added. The mixture was stirred cold 1 hour and at room temperature 1½ hours (became a clear solution near the end of this time). The solution was cooled in an ice bath and a solution of chiral amine prepared in Example 1 Part A(2) (267 mg, 1 mmol) in THF (3 ml) was added. The cooling bath was removed and the mixture was left stirring overnight at room temperature. The solvent was removed in vacuo. $CHCl_3$ (35 ml) was added to the residue. The solution was washed with 1N HCl (15 ml), 1N NaOH (15 ml) and $H_2O$ (15 ml), dried ($MgSO_4$) and freed of solvent in vacuo leaving a very viscous oil (340 mg). This was chromatographed on silica gel (20 g, Baker for flash chromatography), eluting with EtOAc and 5% MeOH in EtOAc to give the title compound as a viscous oil (212 mg, 50%). TLC: silica gel, 5% MeOH in EtOAc, vanillin, $R_f$=0.23.

A(4) [1S-[1α,2β(5Z),3β,4α]]-7-[3-[[[[(Butylamino)carbonyl]amino]acetyl]amino]methyl]-7-oxabicyclo[2.2.1]hept-2-yl]-5-heptenoic acid Part A(3) methyl ester (208 mg, 0.491 mmol) was dissolved in distilled THF (20 ml) and water (4.8 ml) in an argon atmosphere. 1N LiOH solution (4.9 ml) was added and the mixture was stirred at room temperature 5 hours. The mixture was neutralized with 1N HCl solution (4.9 ml) and solid KCl was added. The layers were separated. The aqueous layer was reextracted with $CHCl_3$ (3×25 ml). The combined organic layers (THF and $CHCl_3$) were washed with saturated NaCl solution (15 ml), dried ($MgSO_4$) and freed of solvent in vacuo leaving an oil. This was chromatographed on silica gel (18g), eluting with 4% MeOH in $CH_2Cl_2$ to give the title compound (158 mg, 78.2%) as a white foam. TLC: silica gel, 10% MeOH in $CH_2Cl_2$, vanillin, $R_f$=0.28.

Anal Calcd for $C_{21}H_{35}O_5N_3 \cdot 0.1H_2O$: C, 61.32; H, 8.63; N, 10.21. Found: C, 61.15; H, 8.74; N, 10.23.

B.

[1S-[1α,2β(5Z),3β,4α]]-7-[3-[[[1-Thioxo-2-[(butylaminothiocarbonyl)amino]ethyl]amino]methyl]-7-oxabicyclo[2.2.1]hept-2-yl]-5-heptenoic acid Following the procedure of Example 1 and Example 2 except substituting the above Part B acid compound for the Example 1 Part C acid, and the title compound is obtained.

EXAMPLE 4

[1S-[1α,2β(5Z),3β,4α]]-7-[3-[[1-Thioxo-2-[(Butoxythiocarbonyl)amino]ethyl]amino]methyl]-7-oxabicyclo[2.2.1]hept-2-yl]-5-heptenoic acid

A.

[1S-[1β,2α(5Z),3α,4β]]-7-[3-[[[[(Butoxycarbonyl)amino]acetyl]amino]methyl]-7oxabicyclo[2.2.1]hept-2-yl]-5-heptenoic acid, methyl ester A(1) N-(Butoxycarbonyl)glycine ethyl ester Glycine ethyl ester•HCl (3.5 g, 25 mmol) was suspended in distilled $CH_2Cl_2$ (25 ml) in an argon atmosphere. After cooling to −40° C. distilled $Et_3N$ (7.65 ml, 55 mmol) was added followed by dropwise addition of a solution of distilled n-butyl chloroformate (3.2 ml, ~25 mmol) in $CH_2Cl_2$ (10 ml). After stirring at −40° for 1 hour the mixture was left in a freezer (−5° C.) overnight. The mixture was stirred at −5° to −10° for 1 hour. More $CH_2Cl_2$ was added followed by water (50 ml). The layers were separated. The organic layer was washed with 1N HCl (50 ml), saturated $NaHCO_3$ solution (50 ml) and water (50 ml), dried ($MgSO_4$), and freed of solvent in vacuo leaving 3.129 g of material. This was combined with material from a 5 mmol run and chromatographed on silica gel (100 g, Baker for flash chromatography), eluting with ether-hexane 1:1 to give the title compound as an oil (3.196 g, 52.5%). TLC: silica gel, $Et_2O$-hexane 1:1, PMA, $R_f$=0.34.

A(2) N-(Butoxycarbonyl)glycine

The ethyl ester prepared in part A(1) (3.141 g, 15.47 mmol) was dissolved in 100 ml distilled THF and treated with 1N LiOH solution (40 ml). The mixture was left stirring overnight at room temperature. After acidification with concentrated HCl and addition of solid KCl, the layers were separated. The aqueous layer was reextracted with EtOAc (3×50 ml). The combined organic layers (THF+EtOAc) were washed with saturated NaCl solution (25 ml), dried ($MgSO_4$) and freed of solvent in vacuo leaving the title compound (2.78 g, quant.) which slowly crystallized.

A(3) [1S-[1β,2α(5Z),3α,4β]]-7-[3-[[[[(Butoxycarbonyl)amino]acetyl]amino]methyl]-7-oxabicyclo[2.2.1-]hept-2-yl]-5-heptenoic acid, methyl ester The acid prepared in part A(2) (175.2 mg, 1 mmol) was dissolved in distilled THF (8 ml) in an argon atmosphere. After cooling in an ice bath carbonyldiimidazole (CDI) (162 mg, 1 mmol) was added. The mixture was stirred cold 1 hour and at room temperature 1 hour. The mixture was again cooled in an ice bath and a solution of chiral amine (prepared in Example 1 Part A(2), 267 mg, 1 mmol) in THF (3 ml) was added. The cooling bath was removed and the mixture was left stirring overnight at room temperature. The solvent was removed in vacuo. $CHCl_3$ (35 ml) was added. The solution was washed with 1N HCl (15 ml), 1N NaOH (15 ml) and $H_2O$ (15 ml), dried ($MgSO_4$) and freed of solvent in vacuo. The remaining oil (433 mg) was chromatographed on silica gel (20 g of Baker for flash chromatography) eluting with EtOAc to give partially purified material (291 mg). This was rechromatographed on silica gel (20 g), eluting with $Et_2O$ and 2% MeOH in $Et_2O$ to give the title compound (172 mg, 40.5%) as an oil. Additional material (57 mg, 13.4%) was contaminated with a small amount of slower moving material. TLC: silica gel, 5% MeOH in $Et_2O$, vanillin, $R_f = 0.32$.

B.

[1S-[1β,2α(5Z),3α,4β]]-7-[3-[[[[(Butoxycarbonyl-)amino]acetyl]amino]methyl]-7-oxabicyclo[2.2.1]hept-2-yl]-5-heptenoic acid The methyl ester prepared in Part A (168 mg, 0.396 mmol) was dissolved in distilled THF (16 ml) and water (3.8 ml) in an argon atmosphere and 1N LiOH solution (3.9 ml) was added. The mixture was stirred at room temperature 5½ hours, then neutralized with 1N HCl solution (3.8 ml). After adding solid KCl the layers were separated. The aqueous layer was reextracted with $CHCl_3$ (3×25 ml). The combined organic layers (THF+$CHCl_3$) were washed with saturated NaCl solution (15 ml), dried ($MgSO_4$) and freed of solvent in vacuo leaving an oil (150 mg). This was chromatographed on silica gel (10 g, Baker for flash chromatography) eluting with 4% MeOH in $CH_2Cl_2$ to give 77 mg of material which appeared clean by TLC: silica gel, 10% MeOH in $CH_2Cl_2$, vanillin, $R_f = 0.43$. The material became partially crystalline on standing several days in the cold room. Trituration with $Et_2O$ gave the title compound as a white solid (58.5 mg, 36%) m.p. 104°–106° C.

Anal Calcd for $C_{21}H_{34}O_6N_2$: C, 61.44; H, 8.35; N, 6.82. Found: C, 61.50; H, 8.37; N, 6.98.

C.

[1S-[1α,2β(5Z),3β,4α]]-7-[3-[[1-Thioxo-2-[(Butoxythiocarbonyl)amino]ethyl]amino]methyl]-7-oxabicyclo[2.2.1]hept-2-yl]-5-heptenoic acid Following the procedure of Example 1 Part D (1) and (2) except substituting the Example 4 Part B acid for the Example 1 Part C acid, the title compound is obtained.

EXAMPLE 5

[1S-[1β,2α(5Z),3α,4β]]-7-[3-[[[1-Thioxo-2-[(1-thioxohexyl)amino]propyl]amino]methyl]-7-oxabicyclo[2.2.1]hept-2-yl]-5-heptenoic acid

A.

[1S-[1β,2α(5Z),3α(R),4β]]-7-[3-[[[1-Oxo-2-[(1-Oxohexyl)amino]propyl]amino]methyl]-7-oxabicyclo[2.2.1]hept-2-yl]-5-heptenoic acid A(1) (2R)-2-(Hexanoylamino)propionic acid D-alanine (20 mmol) was dissolved in 1N NaOH solution (40 ml) and $Et_2O$ (40 ml) was added. After cooling in an ice bath a solution of hexanoyl chloride (3.1 ml, 22 mmol) in $Et_2O$ (10 ml) was added dropwise. The mixture was stirred cold for 1 hour. The pH was then adjusted to about 8 by adding 1N NaOH solution (about 3 ml) and the mixture was stirred at room temperature 45 minutes. NaOH solution was added to about pH 9–10. The layers were separated and the aqueous layer was washed with $Et_2O$ (50 ml). After acidification of the aqueous layer with concentrated HCl and saturation with solid KCl, the product was extracted into $CHCl_3$ (3×70 ml). The combined $CHCl_3$ extracts were washed with saturated NaCl solution (25 ml), dried ($MgSO_4$), and freed of solvent leaving the title compound as a white crystalline material (2.45 g, 65.5%) after recrystallization from isopropyl ether (20 ml), m.p. 82°–95° C.

A(2) [1S-[1β,2α(5Z),3α(R),4β]]-7-[3-[[[1-Oxo-2-[(1-Oxohexyl)amino]propyl]amino]methyl]-7-oxabicyclo[2.2.1]hept-2-yl]-5-heptenoic acid, methyl ester Part A(1) acid compound (1 mmol) and chiral amine prepared as described in Example 1 Part A(2) (1 mmol) were coupled using CDI (1 mmol) as described in Example 1. The crude product was chromatographed on silica gel (Baker for flash chromatography) eluting with 2–4% MeOH in $Et_2O$. The eluted product was triturated with $Et_2O$ to give the title methyl ester as a white solid (217 mg, 50%).

TLC: silica gel, 5% MeOH in $Et_2O$, vanillin $R_f = 0.47$.

A(3) [1S-[1β,2α(5Z),3α(R),4β]]-7-[3-[[[1-Oxo-2-[(1-Oxohexyl)amino]propyl]amino]methyl]-7-oxabicyclo[2.2.1]hept-2-yl]-5-heptenoic acid The Part A(2) methyl ester (215 mg, 0.49 mmol) was hydrolyzed with LiOH solution in a THF-water mixture as described in Example 1 Part C. The viscous product was dissolved in EtOAc (~b 2–3 ml). On standing crystalline material was deposited. This was harvested by filtration and washed with $Et_2O$ to give title acid (166.6 mg, 80%), m.p. 101°–103°.

Anal Calcd for $C_{23}H_{38}O_5N_2$: C, 65.37; H, 9.06; N, 6.63. Found: C, 65.30; H. 9.16; N, 6.46.

TLC: Silica gel, 10% MeOH in $CH_2Cl_2$, vanillin, $R_f = 0.48$.

$[\alpha]_D = +25.5°$ (c=1.37, MeOH).

B.

[1S-[1β,2α(5Z),3α,4β]]-7-[3-[[[1-Thioxo-2-[(1-thioxohexyl)amino]propyl]amino]methyl]-7-oxabicyclo[2.2.1]hept-2-yl]-5-heptenoic acid Following the procedure of Examples 1 and 2 except substituting the above Part A(3) acid compound for the Example 1 Part C acid, the title compound is obtained.

EXAMPLE 6

[1S-[1β,2α(5Z),3α,4β]]-7-[3-[[[2-Methyl-2'-[(1-thioxohexyl)amino]-1-thioxopropyl]amino]methyl]-7-oxabicyclo[2.2.1]hept-2-yl]-5-heptenoic acid

A.

[1S-[1β,2α(5Z),3α,4β]]-7-[3-[[[2-Methyl-2-[(1-Oxohexyl)amino]-1-oxopropyl]amino]methyl]-7-oxabicyclo[2.2.1]hept-2-yl]-5-heptenoic acid A(1) 2-(Hexanoylamino)-2-methylpropionic acid 2-Aminoisobutyric acid (2.0 g, 19.4 mmol) and n-hexanoyl chloride (3.0 g, 22.4 mmol) were reacted in the presence of NaOH (1.6 g, 40 mmol) in a mixture of ether and water using the method described in Example 1. The title compound (1.90 g, 49%) was obtained after crystallization from benzene, m.p. 141°-143° C.

A(2) [1S-[1β,2α(5Z),3α,4β]]-7-[3-[[[2-Methyl-2-[(1-Oxohexyl)amino]-1-oxopropyl]amino]methyl]-7-oxabicyclo[2.2.1]hept-2-yl]-5-heptenoic acid, methyl ester Part A(1) compound (1 mmol) was reacted with CDI (1 mmol) and then with chiral amine prepared as described in Example 1 Part A(2) (1 mmol) employing the method described in Example 1 Part B. The crude product was chromatographed on silica gel (25 g, Baker for flash chromatography), eluting with 2% MeOH in Et₂O to give title ester (235 mg, 52%) as white crystalline material.

TLC: silica gel, 5% MeOH in Et₂O, vanillin, $R_f$=0.46.

A(3) [1S-[1β,2α(5Z),3α,4β]]-7-[3-[[[2-Methyl-2-[(1-oxohexyl)amino]-1-oxopropyl]amino]methyl]-7-oxabicyclo[2.2.1]hept-2-yl]-5-heptenoic acid The Part A(2) methyl ester (231 mg, 0.51 mmol) was hydrolyzed with LiOH in a water-THF mixture as described in Example 1 Part C to form the title compound.

B.
[1S-[1β,2α(5Z),3α,4β]]-7-[3-[[[2-Methyl-2'-[(1-thioxohexyl)amino]-1-thioxopropyl]amino]methyl]-7-oxabicyclo[2.2.1]hept-2-yl]-5-heptenoic acid Following the procedure of Examples 1 and 2 except substituting the above Part A(3) acid compound for the Example 1, Part C acid, the title compound is obtained.

EXAMPLE 7

[1S-[1β,2α(5Z),3α,4β]]-7-[3-[[[1-Thioxo-2-[(4-phenylthiobenzoyl)amino]ethyl]amino]methyl]-7-oxabicyclo[2.2.1]hept-2-yl]-5-heptenoic acid A.
[1S-[1β,2α(5Z),3α,4β]]-7-[3-[[[[(4-Phenylbenzoyl)amino]acetyl]amino]methyl]-7-oxabicyclo[2.2.1]hept-2-yl]-5-heptenoic acid, methyl ester A(1) 2-[(4-Phenylbenzoyl)amino]acetic acid Glycine (5 mmol) was reacted with 4-biphenylcarbonyl chloride (about 5 mmol) in the presence of 1N NaOH solution (10 ml), ether (21 ml) and THF (2 ml) using the procedure described in Example 5. Most of the product precipitated as a solid on acidification of the aqueous layer during the work up. This was found to be quite insoluble in CHCl₃ and EtOAc. It was largely dissolved in CH₃CN (~35 ml) and filtered to remove insoluble material. Crystalline acid (0.81 g, 63%) was deposited on cooling, m.p. 207°-218° C. decomp.

A(2) [1S-[1β,2α(5Z),3α,4β]]-7-[3-[[[[(4-Phenylbenzoyl)amino]acetyl]amino]methyl]-7-oxabicyclo[2.2.1]hept-2-yl]-5-heptenoic acid, methyl ester Part A(1) acid (1 mmol) was reacted with carbonyldiimidazole (1 mmol) followed by [1S-[1β,2α(5Z),3α,4β]]-7-[3-(aminomethyl)-7-oxabicyclo[2.2.1]hept-2-yl]-5-heptenoic acid, methyl ester (1 mmole) as in Example 1, Part A(2).

A(3) [1S-[1β,2α(5Z),3α,4β]]-7-[3-[[[[(4-Phenylbenzoyl)amino]acetyl]amino]methyl]-7-oxabicyclo[2.2.1]hept-2-yl]-5-heptenoic acid The Example A(2) methyl ester (141 mg, 0.279 mmole) was hydrolyzed with LiOH as described in Example 1 Part C to give a white solid. This was triturated with EtOAc to give title acid (118 mg, 86%), m.p. 227°-229° dec.

Anal Calcd for $C_{29}H_{34}O_5N_2$: C, 71.00; H, 6.99; N, 5.71. Found: C, 70.90; H, 6.91; N, 5.65.

B.
[1S-[1β,2α(5Z),3α,4β]]-7-[3-[[[1-Thioxo-2-[(4-phenylthiobenzoyl)amino]ethyl]amino]methyl]-7-oxabicyclo[2.2.1]hept-2-yl]-5-heptenoic acid Following the procedure of Examples 1 and 2 except substituting the above Part A(3) acid compound for the Example 1 Part C acid, the title compound is obtained.

EXAMPLE 8

[1S-[1α,2β(5Z),3β,4α]]-7-[3-[[[1-Thioxo-2-[(1-thioxobutyl)amino]ethyl]amino]methyl]-7-oxabicyclo[2.2.1]hept-2-yl]-5-heptenoic acid Following the procedure of Examples 1 and 2 except substituting butanoyl chloride for heptanoyl chloride, the title compound is obtained.

EXAMPLE 9

[1S-[1α,2β(5Z),3β,4α]]-7-[3-[[[1-Thioxo-2-[(1-thioxopropyl)amino]ethyl]amino]methyl]-7-oxabicyclo[2.2.1]hept-2-yl]-5-heptenoic acid Following the procedure of Examples 1 and 2 except substituting propanoyl chloride for heptanoyl chloride, the title compound is obtained.

EXAMPLE 10

[1S-[1α,2β(5Z),3β,4α]]-7-[3-[[[1-Thioxo-2-[(1-thioxo-2-pentenyl)amino]ethyl]amino]methyl]-7-oxabicyclo[2.2.1]hept-2-yl]-5-heptenoic acid Following the procedure of Examples 1 and 2 except substituting 2-pentenoyl chloride for heptanoyl chloride, the title compound is obtained.

EXAMPLE 11

[1S-[1α,2β(5Z),3β,4α]]-7-[3-[[[1-Thioxo-2-[(1-thioxo-3-pentynyl)amino]ethyl]amino]methyl]-7-oxabicyclo[2.2.1]hept-2-yl]-5-heptenoic acid Following the procedure of Examples 1 and 2 except substituting 3-pentynoyl chloride for heptanoyl chloride, the title compound is obtained.

EXAMPLE 12

[1S-[1α,2β(5Z),3β,4α]]-7-[3-[[[1-Thioxo-2-[(1-thioxobenzyl)amino]ethyl]amino]methyl]-7-oxabicyclo[2.2.1]hept-2-yl]-5-heptenoic acid Following the procedure of Examples 1 and 2 except substituting benzoyl chloride for heptanoyl chloride, the title compound is obtained.

EXAMPLE 13

[1S-(1α,2β,3β,4α)]-7-[3-[[[1-Thioxo-2-[(1-thioxoheptyl)amino]ethyl]amino]methyl]-7-oxabicyclo[2.2.1]hept-2-yl]-5-heptanoic acid A.
[1S-(1β,2α,3α,4β)]-7-[3-[[[[(1-Oxoheptyl)amino]acetyl]amino]methyl]-7-oxabicyclo[2.2.1]hept-2-yl]-5-heptanoic acid A(1) [1S-(1β,2α,3α,4β)]-7-[3-(Hydroxymethyl)-7-oxabicyclo[2.2.1]hept-2-yl]-5-heptanoic acid, methyl ester To 800 mg (3.0 mmole) of the [1S-[1α,2β(Z),3β,4α]]-7-[3-(hydroxymethyl)-7-oxabicyclo[2.2.1]hept-2-yl]-5-heptenoic acid, methyl ester dissolved in 120 ml of ethyl acetate was added, under an argon atmosphere, 160 mg of 5% Pd on carbon. The argon atmosphere was exchanged for a slight positive pressure of hydrogen and the reaction was stirred for 8 hours at 25°, filtered through a celite plug and evaporated to provide 730 mg (90%) of the title A compound.

A(2) [1S-(1α,2β,3β,4α)]-7-[3-[[[[(1-Oxoheptyl)amino]acetyl]amino]methyl]-7-oxabicyclo[2.2.1]hept-2-yl]-5-heptanoic acid Following the procedure of Examples 1 and 2 except substituting the Part A(1) alcohol-ester for the alcohol ester employed in Example 1 Part A(1), the title compound is obtained.

B.
[1S-[1α,2β(5Z),3β,4α]]-7-[3-[[[1-Thioxo-2-[(1-thioxoheptyl)amino]ethyl]amino]methyl]-7-oxabicyclo[2.2.1]hept-2-yl]heptanoic acid Following the procedure of Examples 1 and 2 except substituting the above Part A(3) acid compound for the Example 1 Part C acid, the title compound is obtained.

EXAMPLE 14

[1S-(1α,2β,3β,4α)]-7-[3-[[[1-Thioxo-2-[(1-thioxopentyl)ethyl]amino]methyl]-7-oxabicyclo[2.2.1]hept-2-yl]heptanoic acid Following the procedure of Example 13 except substituting pentanoyl chloride for heptanoyl chloride, the title compound is obtained.

EXAMPLE 15

[1S-(1α,2β,3β,4α)]-7-[3-[[[1-Thioxo-2-[(1-thioxo-2-butenyl)amino]ethyl]amino]methyl]-7-oxabicyclo[2.2.1]hept-2-yl]heptanoic acid Following the procedure of Example 13 except substituting butenyl chloride for heptanoyl chloride, the title compound is obtained.

EXAMPLE 16

[1S-[1β,2α(5Z),3α,4β]]-7-[3-[[[1-Thioxo-2-[[(1-thioxo-4-phenyl)butyl]amino]ethyl]amino]methyl]-7-oxabicyclo[2.2.1]hept-2-yl]-5-heptenoic acid A.
[1S-[1β,2α(5Z),3α,4β]]-7-[3-[[[[(1-Oxo-4-phenyl)butyl]amino]acetyl]amino]methyl]-7-oxabicyclo[2.2.1]hept-2-yl]-5-heptenoic acid A(1) 4-Phenylbutanoyl glycine ethyl ester 4-Phenylbutyric acid (2.46 g, 15 mmol) was dissolved in distilled THF (70 ml) in an argon atmosphere. After cooling in an ice bath, carbonyldiimidazole (CDI) (2.43 g, 1.5 mmol) was added and the mixture was stirred cold 1 hour and at room temperature 1 hour. The mixture was then cooled and glycine ethyl ester•HCl (2.09 g, 15 mmol) and distilled Et₃N (2.1 ml, 15 mmol) were added. The mixture was left stirring overnight at room temperature. After removal of the solvent in vacuo, Et₂O (200 ml) was added. The solution was washed with 1N HCl (70 ml), 0.5N NaOH (70 ml) and saturated NaCl solution (70 ml), dried (MgSO₄) and freed of solvent in vacuo leaving title compound (3.13 g, 84%) as white crystalline material. TLC: silica gel, Et₂O, UV; $R_f$ 0.58.

A(2) 4-Phenylbutanoyl glycine

The Part A(1) ester (3.07 g, 12.3 mmol) was hydrolyzed with NaOH (5 g, 125 mmol) in water (60 ml). After stirring at room temperature 6 hours, neutral material was removed by washing with Et₂O (2×50 ml). The aqueous solution was then acidified with concentrated HCl solution. The product was extracted into CHCl₃ (3×60 ml), dried (MgSO₄) and freed of solvent in vacuo leaving a white solid. This was recrystallized from EtOAc (10 ml) to give title compound (2.18 g, 80%), m.p. 99°–101° C.

A(3) [1S-[1β,2α(5Z),3α,4β]]-7-[3-[[[[(1-Oxo-4-phenyl)butyl]amino]acetyl]amino]methyl]-7-oxabicyclo[2.2.1]hept-2-yl]-5-heptenoic acid, methyl ester Part A(2) acid (1 mmol) was reacted with CDI (1 mmol) and then with Example 1 Part A(2) chiral amine (1 mmol) as described in Example 1 Part B(2). The crude product was chromatographed on silica gel (26 g, Baker for flash chromatography) eluting with EtOAc and 2% MeOH in EtOAc to give title compound (337 mg, 72%) as an oil. TLC: silica gel, 2% CH₃OH in EtOAc, Ce(SO₄)₂, $R_f$=0.40.

A(4) [1S-[1β,2α(5Z),3α,4β]]-7-[3-[[[[(1-Oxo-4-phenyl)butyl]amino]acetyl]amino]methyl]-7-oxabicyclo[2.2.1]hept-2-yl]-5-heptenoic acid The Part A(3) methyl ester (336 mg, 0.71 mmol) was hydrolyzed with LiOH in a water-THF mixture as described in Example 1 Part C. The crude crystalline product (300 mg) was recrystallized from a mixture of MeOH and EtOAc to give title compound (247.8 mg, 76%), m.p. 114°–116° C., TLC: silica gel, 2% CH₃OH in EtOAc, Ce(SO₄)₂ $R_f$ 0.20 [α]$_D$= −5.8 (C=1.7, CH₃OH).

Anal calcd for C₂₆H₃₆N₂O₅: C, 68.40; H, 7.95; N, 6.14. Found: C, 68.45; H, 8.03; N, 6.11.

B.
[1S-[1β,2α(5Z),3α,4β]]-7-[3-[[[1-Thioxo-2-[[(1-thioxo-4-phenyl)butyl]amino]ethyl]amino]methyl]-7-oxabicyclo[2.2.1]hept-2-yl]-5-heptenoic acid Following the procedure of Examples 1 and 2 except substituting the above Part A(4) acid compound for the Example 1 Part C acid, the title compound is obtained.

EXAMPLE 17

[1S-[1α,2β(5Z),3β,4α]]-7-[3-[[[1-Thioxo-2-[[(1-thioxo-2-phenylthio)ethyl]amino]ethyl]amino]methyl]-7-oxabicyclo[2.2.1]hept-2-yl]-5-heptenoic acid A.
[1S-[1α,2β(Z),3β,4α]]-7-[3-[[[[(Phenylthio)acetyl]amino]acetyl]amino]methyl]-7-oxabicyclo[2.2.1]hept-2-yl]-5-heptenoic acid A(1) (Phenylthio)acetyl glycine ethyl ester The title ethyl ester was prepared from thiophenoxy acetic acid (15 mmol) and the ethyl ester of glycine•HCl using carbonyldiimidazole (CDI) as described in Example 56, Part A giving 2.95 g (78%) of solid.

A(2) (Phenylthio)acetyl glycine

The Part A(1) ethyl ester was hydrolyzed with aqueous NaOH as described in Example 56 Part B to give the title acid (1.041 g, 92%) as a crystalline material.

A(3) [1S-[1α,2β(Z),3β,4α]]-7-[3-[[[[(Phenylthio)acetyl]amino]acetyl]amino]methyl]-7-oxabicyclo[2.2.1]hept-2-yl]-5-heptenoic acid, methyl ester The Part A(2) acid (1.5 mmol) was reacted with CDI (1.5 mmol) followed by Example 1 Part A(2) chiral amine (1.5 mmol) as described in Example 1 Part B(2). The crude product was chromatographed on silica gel (30 g, Baker for flash chromatography) eluting with EtOAc and 2% MeOH in EtOAc to give title ester as a solid, 523 mg, 73%. TLC: silica gel, 5% MeOH in EtOAc, UV+vanillin, $R_f$ 0.48.

A(4) [1S-[1α,2β(Z),3β,4α]]-7-[3-[[[[(Phenylthio)acetyl]amino]acetyl]amino]methyl]-7-oxabicyclo[2.2.1]hept-2-yl]-5-heptenoic acid The Part A(3) methyl ester (467 mg, 0.98 mmol) was hydrolyzed with 1N LiOH (2 equivalents) as described in Example 1 Part C. The crude product was recrystallized from EtOAc (10 ml) to give title acid (419 mg, 93%), m.p. 126°–128° C. $[α]_D = -5.4°$ (c=0.8, MeOH). TLC: silica gel, 10% MeOH in $CH_2Cl_2$+HOAc (3 drops/10 ml), UV+vanillin, $R_f$ 0.51.

Anal. Calcd for $C_{24}H_{32}O_5N_2S$: C, 62.58; H, 7.00; N, 6.08; S, 6.96. Found: C, 62.49; H, 7.14; N, 6.02; S, 6.91.

B.

[1S-[1α,2β(5Z),3β,4α]]-7-[3-[[[1-Thioxo-2-[[(1-thioxo-2-phenylthio)ethyl]amino]ethyl]amino]methyl]-7-oxabicyclo[2.2.1]hept-2-yl]-5-heptenoic acid Following the procedure of Examples 1 and 2 except substituting the above Part A acid compound for the Example 1, Part C acid, the title compound is obtained.

EXAMPLE 18

[1S-[1α,2β(Z),3β,4α]]-7-[3-[[[1-Thioxo-2-[[(1-thioxo-3-(3-hydroxyphenyl)propyl]amino]ethyl]amino]methyl]-7-oxabicyclo[2.2.1]hept-2-yl]-5-heptenoic acid

A.

[1S-[1α,2β(Z),3β,4α]]-7-[3-[[[[3-(4-Hydroxyphenyl)-1-oxopropyl]amino]acetyl]amino]methyl]-7-oxabicyclo[2.2.1]hept-2-yl]-5-heptenoic acid A(1) 3-(4-Hydroxyphenyl)propanoyl glycine ethyl ester 3-(4-Hydroxyphenyl)propionic acid (2.49 g, 15 mmol) was reacted with glycine ethyl ester hydrochloride in the presence of CDI and $Et_3N$ as described in Example 16 Part A(1). After removal of the solvent the residue was dissolved in $CHCl_3$ and washed with 1N HCl, saturated $NaHCO_3$ solution and saturated NaCl solution. After drying ($MgSO_4$) and removal of the solvent in vacuo crude title ester remained (2.44 g) as a viscous oil. NMR indicated this contained a major impurity but it was used without further purification.

A(2) 3-(4-Hydroxyphenyl)propanoyl glycine

Crude Part A(1) ethyl ester was hydrolyzed with NaOH in water as described in Example 56 Part B to give a white solid (1.37 g). This was recrystallized from EtOAc•MeOH to give the title solid (0.98 g, 29% from starting acid).

A(3) [1S-[1α,2β(Z),3β,4α]]-7-[3-[[[[3-(4-Hydroxyphenyl)-1-oxopropyl]amino]acetyl]amino]methyl]-7-oxabicyclo[2.2.1]hept-2-yl]-5-heptenoic acid, methyl ester Example 1, Part A(2) chiral amine (401 mg, 1.5 mmol) was dissolved in distilled THF (20 ml) in an argon atmosphere. Part A(2) acid (346 mg, 1.55 mmol) was added and the mixture was cooled in an ice bath. Dicyclohexylcarbodiimide (DDC) (319 mg, 1.55 mmol) was added and the mixture was stirred cold 20 minutes and at room temperature overnight. 1N HCl (4 drops) was added and after stirring 10 minutes the solvent was removed in vacuo. EtOAc (8 ml) was added to the residue. After cooling in an ice bath the solid was removed by filtration and washed with cold EtOAc (~10 ml). The filtrate was freed of solvent in vacuo and the remaining material was chromatographed on silica gel (35 g, Baker for flash chromatography) eluting with EtOAc and 3% MeOH in EtOAc to give title ester (243 mg, 34%) as a viscous material. TLC: silica gel, 8% MeOH in EtOAc, UV+vanillin, $R_f$=0.45.

A(4) [1S-[1α,2β(Z),3β,4α]]-7-[3-[[[[3-(4-Hydroxyphenyl)-1-oxopropyl]amino]acetyl]amino]methyl]-7-oxabicyclo[2.2.1]hept-2-yl]-5-heptenoic acid The Part A(3) methyl ester (243 mg, 0.51 mmol) was dissolved in distilled THF (20 ml) and water (2 ml) in an argon atmosphere and treated with 1N LiOH solution (3 ml). The reaction appeared complete by TLC in 1 hour and at 2 hours was worked up as described in Example 1 Part C. The product (212 mg, 90%) was a brittle foam which failed to crystallize. $[α]_D = 5.7°$ (c=0.65, MeOH).

TLC: silica gel, 10% MeOH in $CH_2Cl_2$+HOAc (3 drops/10 ml), UV+vanillin. $R_f$=0.32.

Anal Calcd for $C_{25}H_{34}O_6N_2$: C, 65.48; H. 7.47; N, 6.11. Found: C, 65.34; H, 7.59; N, 6.09.

B.

[1S-[1α,2β(5Z),3β,4α]]-7-(3-[[[1-Thioxo-2-[[(1-thioxo-3-(3-hydroxyphenyl)propyl]amino]ethyl]amino]methyl]-7-oxabicyclo[2.2.1]hept-2-yl]-5-heptenoic acid Following the procedure of Examples 1 and 2 except substituting the above Part A acid compound for the Example 1 Part C acid, the title compound is obtained.

EXAMPLE 19

[1S-[1α,2β(Z),3β,4α]]-7-[3-[[[1-Thioxo-2-phenoxy)ethyl]amino]ethyl]amino]methyl]-7-oxabicyclo[2.2.1]hept-2-yl]-5-heptenoic acid

A.

[1S-[1α,2β(Z),3β,4α]]-7-[3-[[[[(Phenoxyacetyl)amino]acetyl]amino]methyl]-7-oxabicyclo[2.2.1]hept-2-yl]-5-heptenoic acid A(1) Phenoxyacetyl glycine Glycine (20 mmol) was reacted with distilled phenoxyacetyl chloride (22 mmol) in the presence of NaOH (40 mmol) in a mixture of water and ether as described in Example 5 Part A. The crude product was recrystallized from EtOAc (15 ml) to give title acid (2.38 gm, 57%).

A(2) [1S-[1α,2β(Z),3β,4α]]-7-[3-[[[[(Phenoxyacetyl)amino]acetyl]amino]methyl]-7-oxabicyclo[2.2.1]hept-2-yl]-5-heptenoic acid, methyl ester Part A(1) acid (1.5 mmol) was reacted with CDI (1.5 mmol), followed by Example I Part A(2) chiral amine (1.5 mmol) as described in Example 1, Part B. The crude product was chromatographed on silica gel (25 g, Baker for flash chromatography) eluting with EtOAc and 2% MeOH in EtOAc to give title ester as a white solid (463 mg, 67%). TLC: silica gel, 5% MeOH in EtOAc, UV+vanillin, $R_f$=0.53.

A(3) [1S-[1α,2β(Z),3β,4α]]-7-[3-[[[[(Phenoxyacetyl)amino[acetyl]amino]methyl]-7-oxabicyclo[2.2.1]hept-2-yl]-5-heptenoic acid The Part A(2) methyl ester (463 mg, 1.01 mmol) was hydrolyzed with 1N LiOH (2 equivalents) in a THF-$H_2O$ mixture as described in Example 1 Part C to give a white solid. This was recrystallized from EtOAc (20 ml) containing a few drops of MeOH to give title acid (380 mg, 84.6%). $[α]_D = -5.9°$ (c=0.68, MeOH). TLC: Silica gel, 10% MeOH in $CH_2Cl_2$+HOAc (3 drops/10 ml), UV+vanillin, $R_f$=0.57.

Anal Calcd for $C_{24}H_{32}O_6N_2$: C, 64.85; H, 7.26; N, 6.30. Found: C, 64.94; H, 7.34; N, 6.26.

B.

[1S-[1α,2β(5Z),3β,4α]]-7-[3-[[[1-Thioxo-2-[[(1-thioxo-2-phenoxy)ethyl]amino]ethyl]amino]methyl]-7-oxabicyclo[2.2.1]hept-2-yl]-5-heptenoic acid Following the procedure of Examples 1 and 2 except substituting the above Part B acid compound for the Example 1 Part C acid, the title compound is obtained.

EXAMPLE 20

[1S-[1α,2β(5Z),3β,4α]]-7-[3-[[[1-Thioxo-2-[[(1-thioxo-3-phenylpropyl)amino]ethyl]amino]methyl]-7-oxabicyclo[2.2.1]hept-2-yl]-5-heptenoic acid

A.

[1S-[1α,2β(5Z),3β,4α]]-7-[3-[[[[(1-Oxo-3-phenylpropyl)amino]acetyl]amino]methyl]-7-oxabicyclo[2.2.1]hept-2-yl]-5-heptenoic acid A(1) 3-Phenylpropanoyl glycine Glycine (1.5 g, 20 mmol) and hydrocinnamoyl chloride (3.37 g, 22 mmol) were reacted in the presence of NaOH (40 mmol) in a mixture of water and ether using the method described in Example 5 Part A. The crude product was extracted into chloroform, dried ($MgSO_4$) and freed of solvent in vacuo leaving a near white solid (3.53 g, 85%). This was recrystallized from EtOAc (13 ml) to give title compound (2.66 g, 64%) m.p. 112°–114° C.

A(2) [1S-[1α,2β(5Z),3β,4α]]-7-[3-[[[[(1-Oxo-3-phenylpropyl)amino]acetyl]amino]methyl]-7-oxabicyclo[2.2.1]hept-2-yl]-5-heptenoic acid, methyl ester Part A(1) acid (1 mmol) was reacted with CDI (1 mmol) and then with Example 1 Part A(2) chiral amine (1 mmol) as described in Example 1 Part B(2). The crude product was chromatographed on silica gel (25 g, Baker for flash chromatography), eluting with 2% MeOH in EtOAc to give title compound (330 mg, 72%) as an oil. TLC: silica gel, 2% MeOH in EtOAc, vanillin $R_f$=0.29.

A(3) [1S-[1α,2β(5Z),3β,4α]]-7-[3-[[[[(1-Oxo-3-phenylpropyl)amino]acetyl]amino]methyl]-7-oxabicyclo[2.2.1]hept-2-yl]-5-heptenoic acid The Part A(2) methyl ester (330 mg, 0.72 mmol) was hydrolyzed with LiOH in a water-THF mixture as described in Example 1 Part C. The crude crystalline product was recrystallized from EtOAc (12 ml) to give title compound (264 mg, 82.8%) m.p. 119°–122° C. TLC: silica gel, 8% MeOH in $CH_2Cl_2$, UV and vanillin, $R_f$=0.29. $[\alpha]_D$= −5.9 (c=1.1, MeOH).

Anal Calcd for $C_{25}H_{34}O_5N_2$: C, 67.85; H, 7.74; N, 6.33. Found: C, 67.62; H, 7.65; N, 6.22.

B.

[1S-[1α,2β-(5Z),3β,4α]]-7-[3-[[[1-thioxo-2-[[(1-thioxo-3-phenylpropyl)amino]ethyl]amino]methyl]-7-oxabicyclo[2.2.1]hept-2-yl]-5-heptenoic acid Following the procedure of Examples 1 and 2 except substituting the above Part A acid compound for the Example 1 Part C acid, the title compound is obtained.

EXAMPLE 21

[1S-[1α,2β(5Z),3β,4α]]-7-[3-[[[1-Thioxo-2-[(1-thioxo-5-phenylpentyl)amino]ethyl]amino]methyl]-7-oxabicyclo[2.2.1]hept-2-yl]-5-heptenoic acid

A.

[1S-[1α,2β(5Z),3β,4α]]-7-[3-[[[[(1-Oxo-5-phenylpentyl)amino]acetyl]amino]methyl]-7-oxabicyclo[2.2.1]hept-2-yl]-5-heptenoic acid A(1) 5-Phenylpentanoyl glycine ethyl ester 5-Phenylvaleric acid (2.67 g, 15 mmol) in distilled THF was reacted with CDI (15 mmol) followed by glycine ethyl ester•HCl (15 mmol) and ($C_2H_5$)$_3$N (15 mmol) as described in Example 56 Part A. The crude material (3.25 g, 82%) was used without purification.

A(2) 5-Phenylpentanoyl glycine

The Part A(1) ester (12.34 mmol) was hydrolyzed with NaOH in water as described in Example 16 Part A(2). The crude product was recrystallized from EtOAc (12 ml) to give title compound (2.39 g, 82%), m.p. 93°–96° C.

A(3) [1S-[1α,2β(5Z),3β,4α]]-7-[3-[[[[(1-Oxo-5-phenylpentyl)amino]acetyl]amino]methyl]-7-oxabicyclo[2.2.1]hept-2-yl]-5-heptenoic acid, methyl ester Part A(2) compound (1 mmol) was reacted with CDI (1 mmol) and then with Example 1 Part A(2) chiral amine (1 mmol) as described in Example 1 Part B(2). The crude product was chromatographed on silica gel (25 g, Baker for flash chromatography) eluting with 2% MeOH in EtOAc to give title compound (363 mg, 75%) as an oil. TLC: silica gel, 2% MeOH in EtOAc, vanillin $R_f$=0.33.

A(4) [1S-[1α,2β(5Z),3β,4α]]-7-[3-[[[[(1-Oxa-5-phenylpentyl)amino]acetyl]amino]methyl]-7-oxabicyclo[2.2.1]hept-2-yl]-5-heptenoic acid The Part A(3) methyl ester (362 mg, 0.749 mmol) was hydrolyzed with LiOH in a water-THF mixture as described in Example 1 Part C. The crude crystalline product was recrystallized from EtOAc (10 ml) containing a few drops of MeOH to give title compound (278 mg, 79%), m.p. 129°–131° C. TLC: silica gel, 8% MeOH in $CH_2Cl_2$, vanillin, $R_f$=0.31 $[\alpha]_D$= −5.5 (c=0.9, $CH_3OH$).

Anal Calcd for $C_{27}H_{38}O_5N_2$: C, 68.91; H, 8.14; N, 5.95. Found: C, 68.82; H, 8.02; N, 5.88.

B.

[1S-[1α,2β(5Z),3β,4α]]-7-[3-[[[1-Thioxo-2-[(1-thioxo-5-phenylpentyl)amino]ethyl]amino]methyl]-7-oxabicyclo[2.2.1]hept-2-yl]-5-heptenoic acid Following the procedure of Examples 1 and 2 except substituting the above Part A acid compound for the Example 1 Part C acid, the title compound is obtained.

EXAMPLE 22

[1S-[1α,2β(Z),3β,4α]]-7-[3-[[[1-Thioxo-2-[(1-thioxo-4-cyclohexylbutyl)amino]ethyl]amino]methyl]-7-oxabicyclo[2.2.1]hept-2-yl]-5-heptenoic acid

A.

[1S-[1α,2β(Z),3β,4α]]-7-[3-[[[[(4-Cyclohexyl-1-oxobutyl)amino]acetyl]amino]methyl]-7-oxabicyclo[2.2.1]hept-2-yl]-5-heptenoic acid A(1) 4-Cyclohexylbutanoic acid 4-Phenylbutanoic acid prepared as described in Example 16, Part A(1) was dissolved in glacial acetic acid (25 ml). Platinum oxide (0.1 g) was added and the solution was hydrogenated in the Paar shaker at up to 55 p.s.i until hydrogen uptake ceased (6.5 hours). The catalyst was removed by filtration and the acetic acid was removed in vacuo. The product crystallized and was recrystallized from Et$_2$O (20 ml) to give title compound (1.18 g, 77%), m.p. 85°–88° C.

A(2) [1S-[1α,2β(Z),3β,4α]]-7-[3-[[[[(4-Cyclohexyl-1-oxobutyl)amino]acetyl]amino]methyl]-7-oxabicyclo[2.2.1]hept-2-yl]-5-heptenoic acid, methyl ester The Part A (1) acid (341 mg, 1.5 mmol) was dissolved in CHCl$_3$ (10 ml) in an argon atmosphere. The solution was cooled in an ice bath and carbonyldiimidazole (2.43 mg, 1.5 mmol) was added. The mixture was stirred cold 30 minutes and at room temperature 1 hour. The hydrochloride of the chiral amine (prepared as described in Example 1 Part A(2) (456 mg, 1.5 mmol) was added. The solution was cooled in an ice bath and tri-n-butylamine (0.36 ml, 278 mg, 1.5 mmol) was added and the mixture was left stirring overnight at room temperature. More CHCl$_3$ (40 ml) was added and the solution was washed with 1N HCl (20 ml), saturated NaHCO$_3$ solution (20 ml) and saturated NaCl solution (20 ml). After drying (MgSO$_4$), the solvent was removed in vacuo. The product was purified by chromatography on silica gel (30 g of Baker for flash chromatography) eluting with 1% MeOH in EtOAc to give the title methyl ester (661 mg, 92.5%) as an oil which slowly became crystalline. TLC: silica gel, 2% MeOH in EtOAc, vanillin, R$_f$=0.26.

A(3) [1S-[1α,2β(Z),3β,4α]]-7-[3-[[[[(4-Cyclohexyl-1-oxobutyl)amino]acetyl]amino]methyl]-7-oxabicyclo[2.2.1]hept-2-yl]-5-heptenoic acid The Part A(2) methyl ester (661 mg, 1.39 mmol) was hydrolyzed with LiOH as described in Example 1 Part C. The crude crystalline product was recrystallized from EtOAc (15 ml) and MeOH (1 ml) to give title acid compound (542 mg, 84%), m.p. 141°–143° C. [α]$_D$= −6.0° (C=0.96, MeOH).

TLC: silica gel, 10% MeOH in CH$_2$Cl$_2$, vanillin, R$_f$=0.51

Anal Calcd for C$_{26}$H$_{42}$O$_5$N: C, 67.50; H, 9.15; N, 6.06. Found: C, 67.58; H, 9.24; N, 6.05.

B.
[1S-[1α,2β(5Z),3β,4α]]-7-[3-[[[1-Thioxo-2-[(1-thioxo-4-cyclohexylbutyl)amino]ethyl]amino]methyl]-7-oxabicyclo[2.2.1]hept-2-yl]-5-heptenoic acid Following the procedure of Examples 1 and 2 except substituting the above Part A acid compound for the Example 1 Part C acid, the title compound is obtained.

EXAMPLE 23

[1S-[1α,2β(Z),3β,4α]]-7-[3-[[[1-Thioxo-2-[[(1-thioxo-3-phenylthio)propyl]amino]ethyl]amino]methyl]-7-oxabicyclo[2.2.1]hept-2-yl]-5-heptenoic acid A.
[1S-[1α,2β(Z),3β,4α]]-7-[3-[[[[1-Oxo-3-(phenylthio)-propyl]amino]acetyl]amino]methyl]-7-oxabicyclo[2.2.1]hept-2-yl]-5-heptenoic acid A(1) 3-(Phenylthio)propanoic acid, methyl ester Thiophenol (440 mg, 4 mmol) and Et$_3$N (70 μl, 0.5 mmol) were dissolved in CH$_2$Cl$_2$ (5 ml). Methyl acrylate (412 mg, 4.8 mmol) was added dropwise. The reaction was exothermic. After stirring at room temperature for 30 minutes, the excess methyl acrylate was removed in vacuo. TLC: silica gel, Et$_2$O-hexane 1:2, UV R$_f$=0.58. The crude title ester was used without further purification.

A(2) 3-(Phenylthio)propanoic acid

The crude Part A(1) methyl ester (~4 mmole) was treated with 10 ml 1N NaOH and THF (5 ml). After stirring at room temperature 3 hours, ether (30 ml) was added. The layers were separated and the ether layer was reextracted with 1N NaOH solution (10 ml). The combined aqueous layers were washed with Et$_2$O (20 ml) and then acidified with concentrated HCl. The product was extracted with CHCl$_3$ (2×30 ml). The chloroform extracts were washed with saturated NaCl solution (2×20 ml), dried (MgSO$_4$) and freed of solvent in vacuo leaving title acid as a white solid (quant.). This was used without further purification.

A(3) 3-(Phenylthio)propanoyl glycine ethyl ester

Part A(2) acid (0.740 g, 4.06 mmol) was reacted with carbonyldiimidazole (4.06 mmol) followed by glycine ethyl ester•HCl (4.06 mmol) as described in Example 16 Part A(1) to give the title ester (1.00 g, 92%) as crystalline material.

A(4) 3-(Phenylthio)propanoyl glycine

The Part A(3) ethyl ester (0.96 g, 3.6 mmol) was hydrolyzed with NaOH solution as described in Example 16 Part A(2) to give a white solid which was triturated with Et$_2$O to give title acid (0.75 g, 87%).

A(5) [1S-[1α,2β(Z),3β,4α]]-7-[3-[[[[1-Oxo-3-(phenylthio)propyl]amino]acetyl]amino]methyl]-7-oxabicyclo[2.2.1]hept-2-yl]-5-heptenoic acid, methyl ester The Part A(4) acid (359 mg, 1.5 mmol) was reacted with carbonyldiimidazole (1.5 mmol) followed by the hydrochloride of Example 1 Part A(2) chiral amine by the procedure described in Example 22 Part A(2). The crude product was chromatographed on silica gel (30 g, Baker for flash chromatography), eluting with 1% MeOH in EtOAc to give the title methyl ester (623 mg, 85%) as an oil. TLC: silica gel, 2% MeOH in EtOAc, UV and vanillin R$_f$=0.21.

A(6) [1S-[1α,2β(Z),3β,4α]]-7-[3-[[[[1-Oxo-3-(phenylthio)propyl]amino]acetyl]amino]methyl]-7-oxabicyclo[2.2.1]hept-2-yl]-5-heptenoic acid The Part A(5) methyl ester (623 mg, 1.285 mmol) was dissolved in THF (25 ml) and H$_2$O (2.5 ml) in an argon atmosphere and treated with 1N LiOH solution (2.6 ml). The mixture was stirred at room temperature for 5 hours and then worked up as described in Example 1 Part C. The crude product was chromatographed on silica gel (20 g, Baker for flash chromatography) eluting with 5% MeOH in CH$_2$Cl$_2$ to give an oil (436 mg, 71%) which crystallized on standing. This was recrystallized from EtOAc (10 ml) to give title acid (136.5 mg, 22%), m.p. 95°–97° C. TLC: silica gel, 10% MeOH in CH$_2$Cl$_2$, R$_f$=0.50. [α]$_D$= −5.3° (c=0.88, MeOH).

Anal Calcd for C$_{25}$H$_{34}$O$_5$N$_2$S: C, 63.27; H, 7.22; N, 5.90; S, 6.76. Found: C, 63.41; H, 7.28; N, 5.94; S, 6.63.

B.
[1S-[1α,2β(5Z),3β,4α]]-7-[3-[[[1-Thioxo-2-[[(1-thioxo-3-phenylthio)propyl]amino]ethyl]amino]methyl]-7-oxabicyclo[2.2.1]hept-2-yl]-5-heptenoic acid Following the procedure of Examples 1 and 2 except substituting the above Part A acid compound for the Example 1 Part C acid, the title compound is obtained.

EXAMPLE 24

[1S-[1α,2β(Z),3β,4α]]-7-[3-[[[1-Thioxo-2-[[(1-thioxo-2-phenylmethylthio)ethyl]amino]ethyl]amino]methyl]-7-oxabicyclo[2.2.1]hept-2-yl]-5-heptenoic acid

A.

[1S-[1α,2β(Z),3β,4α]]-7-[3-[[[[[(Phenylmethyl)thio]acetyl]amino]acetyl]amino]methyl]-7-oxabicyclo[2.2.1]hept-2-yl]-5-heptenoic acid A(1) Chloroacetyl glycine Glycine (1.5 g, 20 mmol) was dissolved in 2N NaOH (25 ml, 50 mmol) and ether (20 ml) was added. Chloroacetyl chloride (2.26 g) dissolved in Et$_2$O (20 ml) was added dropwise at 0° C. The mixture was stirred at 0° for 30 minutes and at room temperature 1 hour. The layers were separated and the water layer was washed with Et$_2$O (2×20 ml). The water layer was then acidified to pH 2 with concentrated HCl and the product was extracted into EtOAc (3×50 ml). The combined EtOAc extracts were washed with brine, dried (MgSO$_4$), and freed of solvent in vacuo to give title acid compound as a solid (2.56 g, 84%) which was used without further purification.

A(2) (Benzylthio)acetyl glycine

Part A(1) acid (1.28 g, 8.4 mmol) was dissolved in methanol (10 ml) and cooled in an ice bath. Sodium methoxide (1.08 g, 20 mmol) was added followed by dropwise addition of benzyl mercaptan (1.25 g, 10.08 mmoles). After stirring overnight at room temperature, 1N NaOH solution (10 ml) was added. Ether washes (2×40 ml) removed neutral material. The aqueous layer was then acidified to pH 2 with concentrated HCl. The product was extracted with Et$_2$O (3×50 ml), washed with brine, dried (MgSO$_4$) and freed of solvent in vacuo leaving a white solid. This was recrystallized from benzene to give title acid compound (1.28 g, 64%).

A(3) [1S-[1α,2β(Z),3β,4α]]-7-[3-[[[[[(Phenylmethyl)thio]acetyl]amino]acetyl]amino]methyl]-7-oxabicyclo[2.2.1]hept-2-yl]-5-heptenoic acid, methyl ester Part A(2) acid (359 mg, 1.5 mmol) was reacted with carbonyldiimidazole (1.5 mmol) followed by Example 1 Part A(2) chiral amine•HCl 3 (1.5 mmol) using the procedure described in Example 22. The crude product was chromatographed on silica gel (30 g, Baker for flash chromatography) eluting with 1% MeOH in EtOAc to give title ester as an oil (625 mg, 85%). TLC: silica gel 2% MeOH in EtOAc, UV+vanillin, R$_f$=0.30.

A(4) [1S-[1α,2β(Z),3β,4α]]-7-[3-[[[[[(Phenylmethyl)thio]acetyl]amino]acetyl]amino]methyl]-7-oxabicyclo[2.2.1]hept-2-yl]-5-heptenoic acid The Part A(3) methyl ester (625 mg, 1.28 mmol) was hydrolyzed with 1N LiOH solution (2.6 ml) in a THF-water mixture as described in Example 1 Part C. The reaction mixture was worked up at 5 hours 20 minutes. The crude product was recrystallized from EtOAc (15 ml) to give title product (427 mg, 77.7%), m.p. 98°-101° C. [a]$_D$=−5.7° (c=0.95, MeOH) TLC: silica gel, 10% MeOH in CH$_2$Cl$_2$, UV+vanillin, R$_f$=0.4.

Anal Calcd for C$_{25}$H$_{34}$O$_5$N$_2$S: C, 63.27; H, 7.22; N, 5.90; S, 6.76. Found: C, 63.53; H, 7.42; N, 5.91; S, 6.77.

B.

[1S-[1α,2β(5Z),3β,4α]]-7-[3-[[[1-Thioxo-2-[[(1-thioxo-2-phenylmethylthio)ethyl]amino]ethyl]amino]methyl]-7-oxabicyclo[2.2.1]hept-2-yl]-5-heptenoic acid Following the procedure of Examples 1 and 2 except substituting the above Part A acid compound for the Example 1 Part C acid, the title compound is obtained.

EXAMPLE 25

[1S-[1α,2β(Z),3β,4α]]-7-[3-[[[1-Thioxo-2-[[(1-thioxo-2-(butylthio)ethyl]amino]ethyl]amino]methyl]-7-oxabicyclo[2.2.1]hept-2-yl]-5-heptenoic acid

A.

[1S-[1α,2β(Z),3β,4α]]-7-[3-[[[[[(Butylthio)acetyl]amino]acetyl]amino]methyl]-7-oxabicyclo[2.2.1]hept-2-yl]-5-heptenoic acid A(1) (Butanethio)acetyl glycine Example 24 Part A(1) acid compound (1.28 g, 8.4 mmol) was reacted with 1-butanethiol using the procedure described in Example 24. The crude product was crystallized with diisopropylether (~10 ml) to give title acid (0.55 g, 32%).

A(2) [1S-[1α,2β(Z),3β,4α]]-7-[3-[[[[[(Butylthio)acetyl]amino]acetyl]amino]methyl]-7-oxabicyclo[2.2.1]-hept-2-yl]-5-heptenoic acid, methyl ester Part A(1) acid (308 mg, 1.5 mmol) was reacted with carbonyldiimidazole (1.5 mmol) followed by Example 1 Part A(2) chiral amine hydrochloride (1.5 mmol) using the procedure described in Example 22. The crude product was chromatographed on silica gel (30 g, Baker for flash chromatography) eluting with 1% MeOH in EtOAc to give title compound (538 mg, 79%) as an oil. TLC: silica gel, 2% MeOH in EtOAc, UV+vanillin, R$_f$=0.29.

A(3) [1S-[1α,2β(Z),3β,4α]]-7-[3-[[[[[(Butylthio)acetyl]amino]acetyl]amino]methyl]-7-oxabicyclo[2.2.1]hept-2-yl]-5-heptenoic acid The Part A(2) methyl ester (538 mg, 1.18 mmol) was hydrolyzed with 1N LiOH solution (2.4 ml) in a tetrahydrofuran-water mixture using the procedure described in Example 1 Part C. The reaction mixture was worked up in 5 hours. The crude product was crystallized from EtOAc (20 ml) to give title product (444 mg, 85.4%), m.p. 114°-116°. [α]$_D$=−6.0° (c=0.9, MeOH) TLC: silica gel, 10% MeOH in CH$_2$Cl$_2$, UV+vanillin, R$_f$=0.3.

Anal calcd for C$_{22}$H$_{36}$O$_5$N$_2$S: C, 59.97; H, 8.24; N, 6.36; S, 7.28. Found: C, 59.77; H, 8.31; N, 6.30; S, 7.27.

B.

[1S-[1α,2β(5Z),3β,4α]]-7-[3-[[[1-Thioxo-2-[[(1-thioxo-2-butylthio)ethyl]amino]ethyl]amino]methyl]-7-oxabicyclo[2.2.1]hept-2-yl]-5-heptenoic acid Following the procedure of Examples 1 and 2 except substituting the above Part A acid compound for the Example 1 Part C acid, the title compound is obtained.

EXAMPLE 26

[1S-[1α,2β(Z),3β,4α]]-7-[3-[[[1-Thioxo-2-[[(1-thioxo-2-(cyclohexylmethylthio)ethyl]amino]ethyl]amino]methyl]-7-oxabicyclo[2.2.1]hept-2-yl]-5-heptenoic acid

A.

[1S-[1α,2β(Z),3β,4α]]-7-[3-[[[[[(Cyclohexylmethyl)thio]acetyl]amino]acetyl]amino]methyl]-7-oxabicyclo[2.2.1]hept-2-yl]-5-heptenoic acid A(1) Cyclohexylmethylthio acetate Cyclohexylmethyl mesylate (1.92 g, 10 mol) and $KSCOCH_3$ (1.25 g) were suspended in distilled tetrahydrofuran (THF). The reaction mixture was heated under reflux for 3 hours. Additional $KSCOCH_3$ (1.25 g) and THF (9 ml) were added and the mixture was heated under reflux an additional 3 hours. $Et_2O$ (100 ml) was added and the mixture was washed with brine (30 ml). The aqueous layer was reextracted with $Et_2O$ (30 ml). The combined organic layers were washed with brine (15 ml), dried ($MgSO_4$) and freed of solvent to give a straw colored oil (1.8 g). This was chromatographed on silica gel (50 g, Baker for flash chromatography) eluting with 2% $Et_2O$ in hexane to give title compound (1.189 g, 69%) as an oil. TLC: silica gel, 10% $Et_2O$ in hexane, UV and $I_2$, $R_f=0.48$.

A(2) [(Cyclohexylmethyl)thio]acetyl glycine

Part A(1) compound (6 mmol) and the Example 24 Part A(1) acid (6 mmol) were reacted in the presence of NaOMe (17 mmol) as described in Example 24 Part A(2). The crude product was crystallized from diisopropyl ether to give title compound (516 mg, 35%).

A(3) [1S-[1α,2β(Z),3β,4α]]-7-[3-[[[[[(Cyclohexylmethyl)thio]acetyl]amino]acetyl]amino]methyl]-7-oxabicyclo[2.2.1]hept-2-yl]-5-heptenoic acid, methyl ester Part A(2) compound (368 mg, 1.5 mmol) was coupled with Example 1 Part A(2) chiral amine•HCl (456 mg, 1.5 mmol) in the presence of carbonyl diimidazole (CDI) (1.5 mmol) as described in Example 22 Part A(2). The crude product was chromatographed on silica gel (30 g, Baker for flash chromatography) eluting with 1% MeOH in EtOAc to give title compound (542 mg, 73%) as an oil. TLC: silica gel, 2% MeOH in EtOAc, UV+vanillin, $R_f=0.38$.

A(4) [1S-[1α,2β(Z),3β,4α]]-7-[3-[[[[[(Cyclohexylmethyl)thio]acetyl]amino]acetyl]amino]methyl]-7-oxabicyclo[2.2.1]hept-2-yl]-5-heptenoic acid The Part A(3) methyl ester (542 mg, 1.09 mmol) was hydrolyzed with 1N LiOH (4 ml) in a mixture of THF and water as described in Example 1 Part C. The crude product was recrystallized from EtOAc (30 ml) to give title acid (439 mg, 83%), m.p. 131°–133° C. TLC: silica gel, 10% MeOH in $CH_2Cl_2$, UV+vanillin, $R_f=0.56$. $[\alpha]_D=-5.0°$ (c=0.95, MeOH).

Anal Calcd for $C_{25}H_{40}N_2O_5S$: C, 62.47; H, 8.39; N, 5.83; S, 6.67. Found: C, 62.37; H, 8.46; N, 5.77; S, 6.60.

[1S-[1α,2β(5Z),3β,4α]]-7-[3-[[[1-Thioxo-2-[[(1-thioxo-2-(cyclohexylmethylthio)ethyl]amino]ethyl]amino]methyl]-7-oxabicyclo[2.2.1]hept-2-yl]-5-heptenoic acid Following the procedure of Examples 1 and 2 except substituting the above Part A acid compound for the Example 1 Part C acid, the title compound is obtained.

EXAMPLE 27

[1S-[1α,2β(Z),3β,4α]]-7-[3-[[[1-Thioxo-2-[[(1-thioxo-2-phenylsulfinyl)ethyl]amino]ethyl]amino]methyl]-7-oxabicyclo[2.2.1]hept-2-yl]-5-heptenoic acid

A.

[1S-[1α,2β(Z),3β,4α]]-7-[3-[[[[[(Phenylsulfinyl)acetyl]amino]acetyl]amino]methyl]-7-oxabicyclo[2.2.1]hept-2-yl]-5-heptenoic acid Powdered $NaIO_4$ (385 mg, 1.8 mmol) was dissolved in water (12 ml). A solution of Example 17 Part A acid compound (276 mg, 0.6 mmol) in methanol (20 ml) was added. The mixture was stirred overnight at room temperature. Most of the methanol was removed in vacuo. Saturated NaCl solution (50 ml) was added. The product was extracted with $CHCl_3$ (3×50 ml). The combined chloroform extracts were washed with NaCl solution (20 ml), dried ($MgSO_4$), and freed of solvent in vacuo leaving an oil. This was chromatographed on silica gel (4 g, Baker for flash chromatography) eluting with 5% MeOH in $CH_2Cl_2$ to give a foam (254 mg) which gave vary broad peaks in $^1H$ NMR. The material was dissolved in $CHCl_2$ (100 ml) and washed with 1N HCl solution (2×25 ml) and saturated NaCl solution (2×20 ml), dried ($MgSO_4$) and freed of solvent in vacuo leaving title acid (213 mg, 74%) as a white solid foam. TLC: silica gel, 10% MeOH in $CH_2Cl_2$, UV+vanillin, $R_f=0.14$.

Anal calcd for $C_{24}H_{32}N_2O_6S \cdot 0.2H_2O$: C, 60.02; H, 6.80; N, 5.83; S, 6.68. Found: C, 59.95; H, 6.83; N, 5.78; S, 6.53.

B.

[1S-[1α,2β(Z),3β,4α]]-7-[3-[[[1-Thioxo-2-[[(1-thioxo-2-phenylsulfinyl)ethyl]amino]ethyl]amino]methyl]-7-oxabicyclo[2.2.1]-hept-2-yl]-5-heptenoic acid Following the procedure of Example 17B except substituting the above Part A acid for the Example 17, Part A acid, the title compound is obtained.

EXAMPLE 28

[1S-[1α,2β(Z),3β,4α]]-7-[3-[[[1-Thioxo-2-[[(1-thioxo-2-phenylsulfonyl)ethyl]amino]ethyl]amino]methyl]-7-oxabicyclo[2.2.1]hept-2-yl]-5-heptenoic acid

A.

[1S-[1α,2β(Z),3β,4α]]-7-[3-[[[[[(Phenylsulfonyl)acetyl]amino]acetyl]amino]methyl]-7-oxabicyclo[2.2.1]hept-2-yl]-5-heptenoic acid Example 17 Part A acid compound (44.5 mg, 0.9 mmol) was dissolved in methanol (10 ml) and cooled in an ice bath. Oxone (810 mg ~2.7 mmol) dissolved in water (10 ml) was added. The mixture was stirred at room temperature 4 hours, then diluted with water (30 ml). The product was extracted into $CHCl_3$ (3×35 ml). The combined $CHCl_3$ extracts were washed with saturated NaCl solution (2×20 ml), dried ($MgSO_4$), and freed of solvent in vacuo leaving an oil (430 mg). This was chromatographed on silica gel (10 g, Baker for flashed chromatography) eluting with 5% MeOH in $CH_2Cl_2$ to give title acid, 165 mg (37%). TLC: silica gel, 10% MeOH/$CH_2Cl_2$, UV+vanillin. $R_f=0.27$.

Anal Calcd for $C_{24}H_{32}O_7N_2S \cdot 0.5H_2O$: C, 57.46; H. 6.63; N, 5.59. Found: C, 57.27; H, 6.44; N, 5.55.

B.
[1S-[1α,2β(Z),3β,4α]]-7-[3-[[[1-Thioxo-2-[[(1-thioxo-2-phenylsulfonyl)ethyl]amino]ethyl]amino]methyl]-7-oxabicyclo[2.2.1]hept-2-yl]-5-heptenoic acid Following the procedure of Example 17 Part B except substituting the above Part A acid for the Example 17, Part A acid, the title compound is obtained.

EXAMPLE 29

[1S-[1β,2α(Z),3β,4α]-6-[3-[[[1-Thioxo-2-[(1-thioxoheptyl)amino]ethyl]amino]methyl]-7-oxabicyclo[2.2.1-]hept-2-yl]-1-(1H-tetrazol-5-yl)-4-hexene

A.
[1S-[1β,2α(Z),3α,4β]]-6-[3-[[[[(1-Oxohexyl)amino]acetyl]amino]methyl]-7-oxabicyclo[2.2.1]hept-2-yl]-1-(1H-tetrazol-5-yl)-4-hexene A(1) [1S-[1β,2α(Z),3α,4β]]-6-[3-Hydroxymethyl-7-oxabicyclo[2.2.1]hept-2-yl]-1-(1H-tetrazol-5-yl)-4-hexene To 5.5 g (11.8 mmole) of triphenyl-4-(1H-tetrazol-5-yl)butyl phosphonium bromide in 100 ml of tetrahydrofuran (THF) at 0° is added 2.78 g (23.6 mmole) potassium t-butoxide. The reaction is stirred at 25° for 30 minutes and (exo)octahydro-5,8-epoxy-1H-benzopyran-3-ol, (2 g, 11.8 mmole, prepared as described in U.S. Pat. No. 4,143,054) is added in 30 ml of THF. The reaction is stirred for 2 hours and quenched with dilute aqueous HCl. The aqueous layer is extracted with 250 ml of ethyl acetate. The combined organic solutions are evaporated in vacuo, diluted with 500 ml of a 5% NaHCO₃ solution, washed with 100 ml of ether, acidified with dilute HCl to pH 3, and extracted with three 500 ml portions of ethyl acetate. The combined organic solutions are dried over anhydrous MgSO₄, and purified by silica chromatography using a 5% methanol in methylene chloride eluant to provide title A compound.

A(2) [1S-[1β,2α(Z),3α,4β]]-6-[3-[[[[(1-Oxohexyl)amino]acetyl]amino]methyl]-7-oxabicyclo[2.2.1]hept-2-yl]-1-(1H-tetrazol-5-yl)-4-hexene Following the procedure of Examples 1 and 2 except substituting the Part A(1) compound for the hydroxymethyl compound used in Example 1 Part A(2), the title compound is obtained.

B.
[1S-[1β,2α(Z),3α,4β]]-6-[3-[[[1-Thioxo-2-[(1-thioxoheptyl)amino]ethyl]amino]methyl]-7-oxabicyclo[2.2.1-]hept-2-yl]-1-(1H-tetrazol-5-yl)-4-hexene Following the procedure of Examples 1 and 2 except substituting the above Part A acid compound for the Example 1 Part C acid, the title compound is obtained.

EXAMPLES 30 TO 65

Following the procedures outlined in the specification and described in the above working Examples, the following compounds may be prepared.

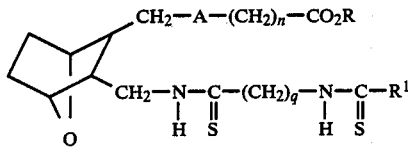

| Ex. No. | A | (CH₂)ₙ | R | (CH₂)_q | R¹ |
|---|---|---|---|---|---|
| 30. | CH=CH | $\overset{CH_3}{\underset{}{-CH-}}$ | CO₂H | (CH₂)₇ | $-CH_2-\overset{H}{\underset{}{C}}=\overset{H}{\underset{}{C}}-CH_3-$ |
| 31. | (CH₂)₂ | $\overset{CH_3}{\underset{CH_3}{-C-}}$ | CO₂H | $\overset{CH_3}{\underset{}{-CH-}}$ | OC₆H₅ |
| 32. | (CH₂)₂ | (CH₂)₄ | CO₂H | —CH₂— | C₆H₅ |
| 33. | CH=CH | $\overset{CH_3\ \ CH_3}{\underset{}{-C-CH_2-}}$ | CO₂H | $\overset{CH_3}{\underset{}{-CH_2-CH-}}$ | CH₂C₆H₅ |
| 34. | CH=CH | $\overset{CH_3\ \ CH_3}{\underset{}{-CH-CH-}}$ | CO₂H | $\overset{CH_3\ \ CH_3}{\underset{}{-CH_2-C-}}$ | —(CH₂)₂C₆H₅ |
| 35. | (CH₂)₂ | $\overset{CH_3}{\underset{F}{-C-CH_2-}}$ | $\overset{N-N}{\underset{N-N}{\underset{H}{\|\|}}}\!\!\!\big\langle$ | $\overset{CH_3}{\underset{}{-CH_2-CH-CH_2-}}$ | —C₆H₄—p-CH₃ |
| 36. | CH=CH | $\overset{F\ \ F}{\underset{}{-CH-CH-}}$ | CO₂H | —(CH₂)₃— | —C₆H₄—p-OH |
| 37. | (CH₂)₂ | $\overset{F\ \ F}{\underset{}{-C-CH_2-}}$ | CO₂H | $\overset{C_2H_5}{\underset{}{-CH_2-CH-}}$ | —OCH₂C₆H₅ |

-continued

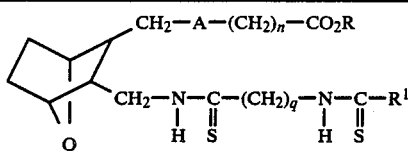

| Ex. No. | A | $(CH_2)_n$ | R | $(CH_2)_q$ | $R^1$ |
|---|---|---|---|---|---|
| 38. | $(CH_2)_2$ | $-(CH_2)_5$ | ![tetrazole-CH3] | $-CH_2-\underset{H}{\overset{CH_3}{C}}-CH_2-$ | $-SC_2H_5$ |
| 39. | CH=CH | $-CH_2-\underset{H}{\overset{CH_3}{CH}}-CH_2-$ | $CO_2C_4H_9$ | $-\underset{CH_3}{\overset{CH_3}{C}}-CH_2-$ | $-OC_6H_5$ |
| 40. | $(CH_2)_2$ | $-CH_2-\underset{}{\overset{CH_3 \; CH_3}{C}}-$ | $CO_2H$ | $(CH_2)_2$ | $-NH_2$ |
| 41. | CH=CH | $CH_2$ | $CO_2H$ | $-CH_2-$ | $-NHCH_3$ |
| 42. | $(CH_2)_2$ | $(CH_2)_2$ | ![tetrazole-CH3] | $-CH_2-\underset{CH_3}{\overset{CH_3}{C}}-$ | $-NHC_6H_5$ |
| 43. | CH=CH | $(CH_2)_3$ | $CO_2H$ | $-CH_2-\underset{}{\overset{CH_3 \; CH_3}{CH-CH}}-CH_2-$ | $-NCH_3(C_2H_5)$ |
| 44. | $(CH_2)_2$ | $(CH_2)_4$ | $CO_2H$ | $(CH_2)_2$ | $-N(CH_3)_2$ |
| 45. | CH=CH | $-CH_2\underset{}{\overset{F \; F}{C}}-$ | ![tetrazole-CH3] | $(CH_2)_3$ | $CH_3$ |
| 46. | $(CH_2)_2$ | $-CH_2-\underset{}{\overset{CH_3 \; CH_3}{C}}-$ | $CO_2H$ | $-\underset{}{\overset{F}{CH}}-CH_2-$ | $-NH-CH_2-C_6H_5$ |
| 47. | CH=CH | $(CH_2)_5$ | $CO_2H$ | $-\underset{}{\overset{F \; F}{C-CH_2}}$ | $-(CH_2)_2CH=CHCH_3$ |
| 48. | $(CH_2)_2$ | $-\underset{}{\overset{CH_3 \; F}{CH-CH}}-$ | $CO_2H$ | $(CH_2)_2$ | $C_6H_5$ |
| 49. | $(CH_2)_2$ | $(CH_2)_2$ | ![tetrazole-CH3] | $CH_2$ | $-CH_2C_6H_5$ |
| 50. | CH=CH | $(CH_2)_3$ | $CO_2H$ | $(CH_2)_3$ | $-SC_4H_9$ |
| 51. | $(CH_2)_2$ | $(CH_2)_4$ | $CO_2H$ | $(CH_2)_8$ | $-SC_6H_5$ |
| 52. | CH=CH | $(CH_2)_5$ | $CO_2H$ | $(CH_2)_{10}$ | $-NCH_3(C_6H_5)$ |
| 53. | CH=CH | $CH_2$ | $CO_2H$ | $(CH_2)_2$ | $CH_3$ |
| 54. | $(CH_2)_2$ | $(CH_2)_2$ | $CO_2H$ | $(CH_2)_3$ | $CH_3$ |
| 55. | CH=CH | $(CH_2)_3$ | ![tetrazole-CH3] | $(CH_2)_4$ | $-CH=CH-CH_3$ |
| 56. | $(CH_2)_2$ | $(CH_2)_4$ | $CO_2H$ | $(CH_2)_5$ | $-C\equiv C-CH_3$ |

-continued

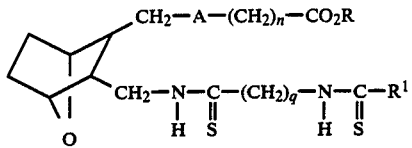

| Ex. No. | A | $(CH_2)_n$ | R | $(CH_2)_q$ | $R^1$ |
|---|---|---|---|---|---|
| 57. | CH=CH | $(CH_2)_5$ | | $(CH_2)_6$ | $-CH_2-C{\equiv}C-CH_3$ |
| 58. | CH=CH | $(CH_2)_3$ | $CO_2H$ | $CH_2$ | $-CH_2-\overset{O}{\underset{\|}{S}}C_6H_5$ |
| 59. | CH=CH | $CH_2$ | $CO_2H$ | $CH_2$ | $-CH_2-\overset{O}{\underset{\|}{S}}C_2H_5$ |
| 60. | $(CH_2)_2$ | $(CH_2)_3$ | $CO_2C_4H_9$ | $(CH_2)_2$ | $-CH_2-\overset{O}{\underset{\|}{S}}CH_2C_6H_5$ |
| 61. | CH=CH | $(CH_2)_3$ | $CO_2H$ | $(CH_2)_3$ | $-CH_2-S-C_2H_5$ |
| 62. | $(CH_2)_2$ | $(CH_2)_3$ | $CO_2H$ | $CH_2$ | $-CH_2-S-CH_2-C_6H_5$ |
| 63. | CH=CH | $(CH_2)_3$ | $CO_2H$ | $CH_2$ | $-CH_2-O-CH_2-C_6H_5$ |
| 64. | CH=CH | $CH_2$ | $CO_2H$ | $CH_2$ | $-CH_2-\underset{H}{N}-CH_2C_6H_5$ |
| 65. | $(CH_2)_2$ | $(CH_2)_3$ | 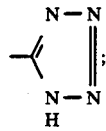 | $(CH_2)_2$ | $-CH_2-S-C_4H_9$ |

What is claimed is:

1. A compound having the structure

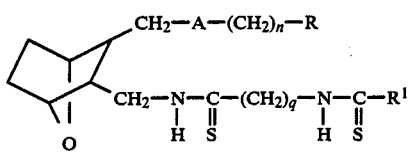

including all stereoisomers thereof, wherein
A is —CH=CH— or —CH$_2$—CH$_2$—; n is 1 to 5;
R is CO$_2$H, CO$_2$alkyl, or

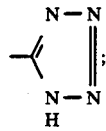

q is 1 to 12; and R$^1$ is H, lower alkyl, lower alkenyl, lower alkynyl, aryl, arylalkyl, lower alkoxy, arylalkoxy, aryloxy, amino, alkylamino, arylamino, arylalkylamino, lower alkyl-S-, aryl-S-, arylalkyl-S-,

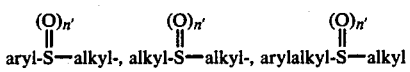

aryl-S—alkyl-, alkyl-S—alkyl-, arylalkyl-S—alkyl wherein n' is 0, 1 or 2), alkylaminoalkyl, arylaminoalkyl, arylalkylaminoalkyl, alkoxyalkyl or arylalkoxyalkyl, wherein lower alkyl or alkyl alone or as part of another group contains 1 to 12 carbons and is unsubstituted or is substituted with halo, CF$_3$, alkoxy, aryl, alkyl-aryl, haloaryl, cycloalkyl, alkylcycloalkyl, hydroxy, alkylamino, alkanoylamino, arylcarbonylamino, nitro, cyano, thiol or alkylthio;

cycloalkyl alone or as part of another group contains 3 to 12 carbons, and which is unsubstituted or substituted with 1 or 2 halogens, 1 or 2 lower alkyl groups, 1 or 2 lower alkoxy groups, 1 or 2 hydroxy groups, 1 or 2 alkylamino groups, 1 or 2 alkanoylamino groups, 1 or 2 arylcarbonyl amino groups, 1 or 2 amino groups, 1 or 2 nitro groups, 1 or 2 cyano groups, 1 or 2 thiol groups and/or 1 or 2 alkylthio groups; and aryl alone or as part of another group is a monocyclic or bicyclic aromatic group containing 6 to 10 carbons in the ring portion and which is unsubstituted or is substituted with 1 or 2 lower alkyl groups, 1 or 2 halogens, 1 or 2 lower alkoxy groups, 1 or 2 hydroxy groups, 1 or 2 alkylamino groups, 1 or 2 alkanoylamino groups, 1 or 2 arylcarbonylamino groups, 1 or 2 amino groups, 1 or 2 nitro groups, 1 or 2 cyano groups, 1 or 2 thiol groups and/or 1 or 2 alkylthio groups.

2. The compound as defined in claim 1 wherein R$^1$ is alkyl, alkoxy or arylthioalkyl.

3. The compound as defined in claim 1 wherein A is CH=CH.

4. The compound as defined in claim 1 wherein 2 to 4.

5. The compound as defined in claim 1 wherein q is 1.

6. The compound as defined in claim 1 wherein R is H.

7. The compound as defined in claim 1 wherein n is 2 to 4, R is $CO_2H$, q is 1, and $R^1$ is alkyl, alkoxy or phenylthiomethyl.

8. The compound as defined in claim 1 having the name [1S-[1β,2α(5Z),3α,4β]]-7-[3-[[[1-thioxo-2-[(1-thioxoheptyl)amino]ethyl]amino]methyl]-7-oxabicyclo[2.2.1]hept-2-yl]-5-heptenoic acid or esters thereof, including all stereoisomers thereof.

9. A method of inhibiting platelet aggregation and/or bronochoconstriction, which comprises administering to the circulatory system of a mammalian host an effective amount of a compound as defined in claim 1 or a pharmaceutically acceptable salt thereof.

10. The method as defined in claim 9 wherein said compound is administered in an amount within the range of from about 1 to about 100 mg/kg.

11. A composition for inhibiting platelet aggregation and/or bronchoconstriction comprising an effective amount of a compound as defined in claim 1 or a pharmaceutically acceptable salt thereof, and a pharmaceutically acceptable carrier therefor.

12. A method of treating peripheral vascular diseases, which comprises topically or systemically administering to a mammalian host an effective amount of a compound as defined in claim 1 or a pharmaceutically acceptable salt thereof.

13. The method as defined in claim 12 wherein said compound is administered in an amount within the range of from about 1 to about 100 mg/kg.

14. A method for treating asthma in a mammalian species in need of such treatment, which comprises administering to a mammalian host an effective amount of a compound as defined in claim 1 or a pharmaceutically acceptable salt thereof.

* * * * *